United States Patent
Ragot et al.

(10) Patent No.: US 10,729,662 B2
(45) Date of Patent: Aug. 4, 2020

(54) PRODUCT COMPRISING A PLANT FOR MEDICINAL, COSMETIC, COLORING OR DERMATOLOGIC USE

(71) Applicants: Schweitzer-Mauduit International, Inc., Alpharetta, GA (US); SWM Luxembourg s.a.r.l., Luxembourg (LU)

(72) Inventors: Philippe Ragot, Le Mans (FR); Esther Pons, Pessac (FR); Bernard Mompon, Vannes (FR); Cedric Rousseau, Le Mans (FR)

(73) Assignees: Schweitzer-Mauduit International, Inc., Alpharetta, GA (US); SWM Luxembourg s.a.r.l., Luxembourg (LU)

( * ) Notice: Subject to any disclaimer, the term of this patent is extended or adjusted under 35 U.S.C. 154(b) by 1038 days.

(21) Appl. No.: 14/462,213

(22) Filed: Aug. 18, 2014

(65) Prior Publication Data

US 2015/0056255 A1    Feb. 26, 2015

Related U.S. Application Data

(60) Provisional application No. 61/867,814, filed on Aug. 20, 2013.

(51) Int. Cl.

| | | |
|---|---|---|
| *A61K 36/00* | (2006.01) | |
| *A61K 9/70* | (2006.01) | |
| *A23F 3/14* | (2006.01) | |
| *A61K 8/97* | (2017.01) | |
| *A23F 3/30* | (2006.01) | |
| *A23F 3/38* | (2006.01) | |
| *A23F 3/34* | (2006.01) | |
| *A23F 5/36* | (2006.01) | |
| *A61K 8/02* | (2006.01) | |
| *A61Q 19/00* | (2006.01) | |
| *A23L 2/395* | (2006.01) | |
| *A23L 27/10* | (2016.01) | |
| *A61K 8/49* | (2006.01) | |
| *A61K 31/522* | (2006.01) | |
| *A61K 36/82* | (2006.01) | |

(52) U.S. Cl.
CPC .............. *A61K 9/7007* (2013.01); *A23F 3/14* (2013.01); *A23F 3/30* (2013.01); *A23F 3/34* (2013.01); *A23F 3/385* (2013.01); *A23F 5/36* (2013.01); *A23L 2/395* (2013.01); *A23L 27/11* (2016.08); *A61K 8/02* (2013.01); *A61K 8/0208* (2013.01); *A61K 8/4953* (2013.01); *A61K 8/97* (2013.01); *A61K 31/522* (2013.01); *A61K 36/00* (2013.01); *A61K 36/82* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | |
|---|---|---|
| 3,353,541 A | 11/1967 | Hind et al. |
| 3,386,449 A | 6/1968 | Hind |
| 3,415,253 A | 12/1968 | Michels et al. |
| 3,420,241 A | 1/1969 | Hind et al. |
| 3,428,053 A | 2/1969 | Schoenbaum et al. |
| 3,467,109 A | 9/1969 | Block et al. |
| 3,483,874 A | 12/1969 | Hind |
| 3,561,451 A | 2/1971 | Jacin et al. |
| 3,760,815 A | 9/1973 | Deszyck |
| 3,847,164 A | 11/1974 | Mattina et al. |
| 3,860,012 A | 1/1975 | Selke |
| 4,182,349 A | 1/1980 | Selke |
| 4,674,519 A | 6/1987 | Keritsis et al. |
| 4,891,232 A | 1/1990 | Dahl |
| 5,099,862 A | 3/1992 | White et al. |
| 5,529,796 A | 6/1996 | Gobbo |
| 5,715,844 A | 2/1998 | Young et al. |
| 5,724,998 A | 3/1998 | Gellatly et al. |
| 5,765,570 A | 6/1998 | Litzinger et al. |
| 6,761,918 B2 | 7/2004 | Pulikkottil et al. |
| 6,818,234 B1 | 11/2004 | Nair et al. |
| 7,001,629 B1 | 2/2006 | Mengal et al. |
| 7,793,585 B2 | 9/2010 | Ramussen |
| 8,499,965 B2 | 8/2013 | Sheffield |

(Continued)

FOREIGN PATENT DOCUMENTS

| | | |
|---|---|---|
| CN | 1329855 A | 1/2002 |
| CN | 1565286 A | 1/2005 |

(Continued)

OTHER PUBLICATIONS

Website document entiltled "Adagioteas: ingenuiTEA" (Available at http://www.adagio.com/teaware/ingenuiTEA-teapot.html). Archived to Oct. 21, 2004. Downloaded May 30, 2017.*
Remington's. "Rennington's Pharmaceutical Science 17th Edition" Gannaro, A. (Ed) pp. 37, 1517-1518 (Year: 1985).*
Blumenthal and al., Herbal Medicine, Expanded Commission E. Monographs, pp. 393-400.

(Continued)

Primary Examiner — Terry A Mckelvey
Assistant Examiner — Russell G Fiebig
(74) Attorney, Agent, or Firm — Dority & Manning, P.A.

(57) ABSTRACT

The present invention relates to a product for at least one of medicinal, cosmetic, coloring or dermatologic use. The product comprises a fibrous plant product and a plant extract which is applied thereto. Further, the invention relates to a corresponding method for producing said product and its use in at least one of medicinal, cosmetic, coloring or dermatologic products or applications or treatments. The plants used may be all plants comprising one or more substances of interest to achieve a desired medicinal, cosmetic, coloring or dermatologic effect.

25 Claims, 16 Drawing Sheets

(56) References Cited

U.S. PATENT DOCUMENTS

| | | |
|---|---|---|
| 8,597,667 B2 | 12/2013 | Mou et al. |
| 8,734,881 B2 | 5/2014 | Yoakim et al. |
| 9,220,296 B2 | 12/2015 | Fall et al. |
| 2002/0132098 A1 | 9/2002 | Miyazawa et al. |
| 2003/0004479 A1 | 1/2003 | Ueda et al. |
| 2003/0113411 A1 | 6/2003 | Rose |
| 2003/0187055 A1 | 10/2003 | Riker |
| 2004/0156920 A1 | 8/2004 | Kane |
| 2004/0180077 A1 | 9/2004 | Riker |
| 2005/0064049 A1* | 3/2005 | Mori .................. A61K 8/97 424/725 |
| 2005/0088632 A1 | 4/2005 | Sadi |
| 2005/0158252 A1 | 7/2005 | Romanowski |
| 2006/0165756 A1 | 7/2006 | Catani |
| 2007/0199453 A1 | 8/2007 | Rasmussen |
| 2007/0243273 A1 | 10/2007 | Dev et al. |
| 2009/0047328 A1 | 2/2009 | Cunningham |
| 2009/0169654 A1 | 7/2009 | Banerjee |
| 2010/0032444 A1 | 2/2010 | Sheffield |
| 2010/0196545 A1 | 8/2010 | Buffet et al. |
| 2010/0210866 A1 | 8/2010 | Toyohara et al. |
| 2010/0233322 A1* | 9/2010 | Fukuda .................. A23F 3/14 426/77 |
| 2011/0020512 A1 | 1/2011 | Masutake |
| 2011/0236502 A1 | 9/2011 | Guillory |
| 2013/0280320 A1 | 10/2013 | Mompon |
| 2014/0224265 A1 | 8/2014 | Rouillard et al. |
| 2014/0295049 A1 | 10/2014 | Ragot et al. |
| 2015/0037389 A1 | 2/2015 | Ragot et al. |
| 2015/0050371 A1 | 2/2015 | Gehling et al. |
| 2015/0056255 A1 | 2/2015 | Ragot et al. |
| 2015/0175810 A1 | 6/2015 | Rieland |
| 2015/0374624 A1 | 12/2015 | Ragot et al. |
| 2016/0255854 A1 | 9/2016 | Rousseau |

FOREIGN PATENT DOCUMENTS

| | | |
|---|---|---|
| CN | 1957777 A | 5/2007 |
| CN | 102919430 | 2/2012 |
| CN | 103054156 | 4/2013 |
| DE | 202010001912 U1 | 3/2011 |
| GB | 1341069 | 12/1973 |
| JP | H 09163930 A | 6/1997 |
| JP | H10304822 | 11/1998 |
| JP | 2001131866 A | 5/2001 |
| JP | 2005119967 | 5/2005 |
| JP | 2005306742 A | 11/2005 |
| JP | 2006050934 A | 2/2006 |
| JP | 2006246817 A | 9/2006 |
| JP | 2006249599 A | 9/2006 |
| JP | 2006256968 A | 9/2006 |
| JP | 2007098152 A * | 4/2007 |
| JP | 2008274535 A | 11/2008 |
| JP | 2011182783 A | 9/2011 |
| KR | 20070090286 | 9/2007 |
| KR | 20100114348 | 10/2010 |
| WO | WO9409653 | 5/1994 |
| WO | WO 0205655 | 1/2002 |
| WO | WO-0205655 A1 * | 1/2002 ............. A23F 3/163 |
| WO | WO03091500 | 11/2003 |
| WO | WO2009022434 | 2/2009 |
| WO | WO2011092852 | 8/2011 |
| WO | WO 2012056141 A2 * | 5/2012 ............... A23F 3/14 |

OTHER PUBLICATIONS

Adams et al., Analysis of the Interactions of Botanical Extract Combinations Against the Viability of Prostate Cancer Cell Lines, Mar. 2003, pp. 117-124.

Lin et al., Inhibition of Helicobacter Pylori and Associated Urease by Oregano and Cranberry Phytochemical Synergies, Applied and Environmental Microbiology, Dec. 2005, vol. 71., No. 12, pp. 8558-8564.

PCT/EP2014/067579 International Search Report and Written Opinion dated Nov. 19, 2014, 13 pages.

Raventos et al., Application and Possibilities of Supercritical $CO_2$ Extraction in Food Procssing Industry: An Overview, Food Science Tech. Int. (2002) vol. 8 (5) pp. 269-284.

Greer, C.C,. A Text-Book of Cooking; J.S. Cushing Co.—Berwick & Smith Co. Norwood, MA 1915, pp. 175-177.

Innovation Food Online, Sodium Alginate; URL<https://innovationinfood.wikispaces.com/Sodium+alginate> Published Jan. 4, 2007 Online, 7 pages with one extra page having google search hit with datestamp.

CN20090097787; Huimin, Y., dated Apr. 2009, English Abstract Only, 2 pages.

SU1161061; Choladze, et al., dated Jun. 1985,English Abstract Only, 2, pages.

Blumenthal et al., Herbal Medicine, Expanded Commission E. Monographs, 2000, pp. 393-400.

Co-pending U.S. Appl. No. 15/053,134, filed Feb. 25, 2016.

Co-pending U.S. Appl. No. 15/506,620, filed Feb. 24, 2017.

* cited by examiner

Curved and perforated base for infusion

Tea discs reservoir

Iced tea shaker

Fill in ice cubes and fresh water (possibility to put the shaker into the fridge in advance when no ice cubes).
Reclose the shaker and shake it like a shaker.

Tea Bar

PRODUCT COMPRISING A PLANT FOR MEDICINAL, COSMETIC, COLORING OR DERMATOLOGIC USE

RELATED APPLICATIONS

The present application claims priority to U.S. Patent Application Ser. No. 61/867,814 filed on Aug. 20, 2013, which is hereby incorporated by reference in its entirety.

FIELD OF THE INVENTION

The present invention relates to a product for at least one of medicinal, cosmetic, coloring or dermatologic use. The product comprises a fibrous plant product and a plant extract which is applied thereto. Further, the invention relates to a corresponding method for producing said product and its use in at least one of medicinal, cosmetic, coloring or dermatologic products or applications or treatments. The plants used may be all plants comprising one or more substances of interest to achieve a desired medicinal, cosmetic, coloring or dermatologic effect.

BACKGROUND OF THE INVENTION

Today, materials originating from a plant are used in many applications. If the use of plant based products is intended, e.g. to color items or hair or food or skin because of a preference for natural ingredients, it usually requires specific conditions, such as solvent types, moisture content, temperatures, pH, etc. and can take a considerable time until the final result. Indeed, when a plant product is applied, e.g. in form of a powder, e.g. on hair or skin, two things take place: an extraction of the substance(s) and its fixation on the hair or skin. Actually, it requires a long contact time to obtain a significant result. Moreover, hair or skin can be damaged by substances in the plant such as traces of heavy metals, pesticides, polyphenols. In addition, the quantity of the substance(s) of interest is not necessarily consistent from one application to another due to the variability of the natural ingredient(s). Hence, applying the same amount of a hair coloring product may lead to different results.

The foregoing example is equally true for other uses of plant materials, such as cosmetic, medicinal or dermatologic uses. So far, many substances from plant materials cannot be used in medicinal or dermatologic applications due to the time required for the substance to unfold its effect. In addition, in many applications the concentration of a substance necessary for a certain medicinal or dermatologic effect cannot be achieved or the administration would become difficult, e.g. due to the size of a tablet. Plant materials may release an insufficient amount of substance(s) and/or have a low release rate. Sublingual administration is very often impossible for the same reason. Moreover, in medicinal or dermatologic uses it may be the case that only the combination of more substances or a complex extract of the plant(s) leads to the desired effect. Sometimes it is not entirely known how this combination works and what substances are necessary to achieve the desired effect. In such cases it is desirable to use most or substantially all substances contained in the respective plant(s). On the other hand, it may be desirable to separate certain desired substances from certain undesired substances such as potentially toxic components of the plant.

There is still a need to improve products originating from plant materials for medicinal or cosmetic or coloring or dermatologic use. In particular, it is desirable to control the amount of substances originating from plant materials as well as conditions and time needed to achieve a desired medicinal or cosmetic or coloring or dermatologic effect.

SUMMARY OF THE INVENTION

The invention relates to a product comprising plant materials as raw materials. In particular, the product may comprise a fibrous plant product and a plant extract. The fibrous plant product may comprise solid parts of a plant and the plant extract may comprise substances extracted from a plant. The fibrous plant product may form a layer on which the plant extract is applied to. The plant extract can form a second layer or at least partially enter or penetrate into the fibrous plant product. Alternatively, the fibrous plant product can have any shape like pieces, sheets or powder and the plant extract can be applied likewise to the fibrous plant product. According to the invention it is possible to first separate substances from one or more plants and combine one or more of the remaining or separated substances subsequently.

In the easiest case one plant is separated into a plant extract and a fibrous plant product. Subsequently the fibrous plant product and the plant extract are combined to obtain a reconstructed or reconstituted version of the original plant with improved properties. For example, certain substances of the original plant may be easily water-soluble and others not. In this way one can accelerate or even control the release or extraction rate of certain substances to achieve a medicinal or cosmetic or coloring or dermatologic effect. Also, there can be higher concentrations of certain or all substances as compared to the natural plant.

The fibrous plant product may have at least partially fibrous properties and can comprise substances from one or more specific parts of one or more plants, e.g. a blend of different plants. Also the plant extract can comprises substances from one or more specific parts of one or more plants, e.g. a blend of different plants. Certain substances can be present only in certain parts of a plant, e.g. in one or more of the root, stem, trunk, caulis, leaf, lamina, fruit, flower, seed or bark of a plant. The plant extract may be soluble, e.g. water-soluble, or dispersible.

The plant extract may comprise one or more substances from one or more types of plants of the fibrous plant product. In other words, the plant(s) used as raw material(s) for the fibrous plant product and the plant extract may at least partially be the same.

The plant can be selected from one or more of herbs, medicinal plants, tea, vegetables, dye plants or spices. Examples of plants that are useful in accordance with the present invention are provided in the detailed description. The lists of plants shall provide an overview of exemplary plants that can be used in connection with the invention. The division of the plants into the respective applications shall not be construed as limiting. Plants of two or more categories may be used together in a product according to the invention.

The plant can also be selected from one or more plants containing anthocyanins or carotinoids, or flavonoids. Basically every plant having one or more desired substances for medicinal or cosmetic or coloring or dermatologic applications can be used as raw material for the product according to the invention. Also, any combination of two or more plants can be used. That is, a product may comprise substances from at least one of medicinal, cosmetic, coloring or dermatologic plants.

The product may comprise a layer of fibrous plant product on which a layer of plant extract is formed. Also, the plant extract can partially or entirely penetrate into the fibrous plant product. Also, a multi-layer product with two or more layers of plant extract can be provided, each layer comprising certain substance(s) to provide a certain effect. Optionally, the layers in the multi-layer product can at least partially penetrate into each other. The plant extract can be applied to the fibrous plant product as a fluid or a gel or a slurry or a powder.

A multi-layer product may comprise at least one fibrous plant product layer on which a layer of plant extract is provided. Additional layers of material, e.g. made from plant fibers and/or cellulosic fibers and/or synthetic fibers, may be applied onto one or both surfaces of the first layer (upper/lower side) as exemplarily illustrated in FIG. 1b. The benefit of such design is to develop and/or improve certain physical product characteristics such as wet strength, tensile strength and/or to enhance product appearance and consumer expectations such as look and feel, color and softness while preserving the active molecules delivery from the reconstituted material. A multi-layer structure may also comprise more layers with plant extract. A multi-layer structure may be used, e.g., in a facial mask, in a bandage, patch or the like.

The fibrous plant product may comprise at least about 30% or at least about 40% or at least about 50% or at least about 60% or at least about 70% or at least about 80% or at least about 90% or about 100% by weight of fibrous plant product from one plant. Similarly, the plant extract may comprise at least about 30% or at least about 40% or at least about 50% or at least about 60% or at least about 70% or at least about 80% or at least about 90% or about 100% by weight of plant extract from one plant.

Depending on the intended use, the product can be a sheet, e.g. a paper like sheet, or a powder or a cream or a slurry or a paste or a foam or a liquid or a tablet or a pellet or a granule. The product can be substantially dry, but can optionally be rehydrated, e.g. before use. For example, for use in a hair coloring, e.g. dyeing, tinting, highlighting or bleaching, a dry coloring powder may be rehydrated with water or other liquids or solvents to obtain a composition to be applied to the hair. A to be rehydrated powder and/or sheet product may also be used in other applications, e.g. cosmetic facial masks or medical woundressing or bandages or the like, where water or other liquids or solvents or mixture of them may be applied onto the product before it is used, e.g. applied onto the skin. Also, should the product be stored or further processed, e.g. finalized or pre-finalized for a specific application, it can be in form of a powder or a sheet for storage or transportation to the finalization process.

The product can be one or more of a drug or medicament, at least one part of a medical device, a cosmetic agent, a coloring agent, a dermatologic agent, an antibacterial agent, an antiviral agent, a fungicide agent, or a germicidal agent. Also, the product can be used in a method for treating a disease or disorder.

The invention further relates to at least one of a pharmaceutical, coloring, cosmetic or dermatologic composition comprising the product according to the invention. The invention also relates to a medical, cosmetic or dermatologic device or a kit of parts comprising the product according to the invention.

The product according to the invention can be used for at least one of a medicinal, cosmetic, coloring or dermatologic application.

The invention further relates to a method of coloring comprising the step of applying the product according to the invention to the surface to be colored. One aspect relates to the coloring of hair or skin, i.e. the product according to the invention is applied to the hair or skin to be colored. Similarly other items such as textiles or food can be colored. The product for coloring may be sheet like or a paste or a slurry or a powder or a foam.

Additionally, the invention relates to a method of treating a disease or disorder comprising the step of administering the product of the invention. Besides well known forms of administering plant material also sublingual or transdermal administration or administration via a chewing gum is possible as substances cannot only be concentrated but also be released faster than from known products.

The invention also relates to a method for producing a product according to the invention. The method may comprise the steps of:
a) extracting one or more substances of at least one plant to obtain a plant extract;
b) separating the plant extract from the at least partially fibrous residue;
c) optionally refining the residue;
d) preparing a sheet like product from at least a part of the residue;
e) optionally concentrating or purifying or aromatizing the plant extract;
f) applying the plant extract of step b) or e) to the sheet of step d); and
g) optionally drying the product of step f)

It is also possible to select one or more substances or parts from the residue before a product is prepared in step d). Step e) optionally also comprises the selection of certain substances and the filtering of undesired substances. The selection of plants is similar to the respective discussion relating to the product.

In step a) a solvent can be used to extract the one or more substances. A solvent can be any known solvent, such as a polar protic, apolar protic, polar aprotic, apolar aprotic solvent. Also a combination of solvents can be used. The one or more solvents can be determined based on the plant(s) to be processed and the substance(s) to be extracted. Alternatively or in addition to a solvent, extracting the one or more substances can be achieved by mechanical force. To extract substance(s) via mechanical force the plant(s) can be pressed by any known mechanical press or by altering the ambient pressure. Depending on the plant(s) and the substance(s) to be extracted even a simple filtering can be used alone or in addition to solvent(s) or mechanical force as some plants, e.g. after cutting, liberate substances, e.g. in form of liquids. Other filtering means can be used in combination with mechanical vibration, e.g. to separate solid substances such as pollen, from a plant.

The extracting step can be performed using components of a single plant or of a blend of plants. Also, as explained in combination with the product, one or more specific parts of plants can be used.

The at least partially fibrous residue can be mixed with an at least partially fibrous part of at least one further plant prior to preparing the sheet. In this way substances from different origin and with different properties, e.g. mechanical or pharmaceutical, can be mixed together to obtain desired product properties. Also, the at least partially fibrous residue can be mixed with a stabilizer prior to preparing the sheet. For example, the fibrous residue can be mixed with synthetic fibers and/or natural fibers to obtain certain mechanical properties, wherein the fibers are preferably non soluble and/or are approved by food, medicinal and/or cosmetic laws.

The plant extract of step b) or e) can be mixed with a plant extract of at least one further plant prior to applying the plant extract to the sheet. Also, the plant extract of step b) or e) can be mixed with a texturing agent prior to applying the plant extract to the sheet. Texturing agents, e.g. emulsifiers or stabilizers or phosphates or dough conditioners, can be used to add or modify the overall texture, color, mouthfeel or surface of products.

The method may further comprise the step of adding ingredients or removing ingredients, e.g. undesired compounds or impurities, from the plant extract prior to applying the plant extract of step b) or step e) to the sheet of step d). Similarly the method may further comprise the step of adding or removing ingredients from the at least partially fibrous residue prior to applying the plant extract of step b) or step e) to the sheet of step d).

The composition of step g) can be further processed to obtain regularly or irregularly shaped forms or a powder or a cream or a slurry or a paste or a foam or a liquid or a pellet or a granule. In case a product contains a liquid content, e.g. a paste, a certain amount or substantially the entire plant extract may be solved or extracted from the fibrous plant product or respective pieces of fibrous plant product. In other words, further processing the composition of step g) by adding a fluid may change the appearance but the advantages of the reconstituted product according to the invention remain.

The invention further relates to a method of producing a coloring matter according to the method as explained above and optionally further comprising the step of processing the sheet like product to obtain a powder or a paste or a cream or a slurry. Exemplary processing steps may comprise cutting or grinding. The powder may be further processed, e.g. to obtain a paste or cream or slurry. The latter step may be accomplished by adding a fluid to the powder. As explained, even if some or substantially all substances are released from the fibrous plant product, the product according to the invention still provides all advantages as all substances are still present, e.g. in the paste.

The basic idea of the invention is to process one or more plants to obtain an at least partially fibrous residue and a plant extract. Both the fibrous residue and the plant extract can be processed and finally combined to obtain a reconstituted plant product, the properties of which can be controlled depending on the amount and type of substances used. Also other materials not originating from a plant can be added to alter the properties of the resulting product, e.g. to obtain certain mechanical properties or to add a flavor or to improve control of the releasing rate of all or certain substances.

DETAILED DESCRIPTION OF THE INVENTION

Figure 1A:
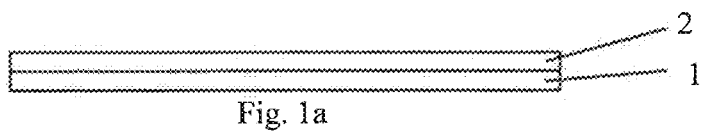
FIG. 1a is a schematic cross sectional view of one exemplary product of the invention.

FIG. 1a shows a schematic cross sectional view of a product according to the invention. The first layer 1 comprises a fibrous plant product and the second layer 2 comprises a plant extract. The first layer may have a thickness of 100 μm to 0.5 cm, preferably 0.2 mm to 5 mm. Instead of having two substantially separate layers, the plant extract can partially or entirely enter or penetrate into the fibrous plant product. The first layer 1 can have a porous structure to facilitate that the plant extract enters into the fibrous plant product. Also, the fibrous plant product can be small pieces of any shape or a paste or a powder and the plant extract can be applied to the plant product.

The product according to the invention may comprise two, three, four, five or more layers, e.g. a first layer 1 comprising a fibrous plant product, a second layer 2 comprising a plant extract with first substance(s), a third layer (not shown) comprising a plant extract with second substance(s), etc. Each layer may comprise different substance(s) offering a specific effect. Also, additional layers or respective substances in the existing layers can be provided for controlling the sequence and/or amount and/or speed substances are released from the product.

One or both of the plant extract and the fibrous plant product may further comprise a matrix of a texturizing agent, such as a non crosslinked hydrocolloid polymer of natural or synthetic origin, preferably of natural origin. The texturizing agent can be selected from at least one of:
- natural agents of plant origin such as carob gum, guar gum, pectins, alginates, carrageenans, agar-agar, gum arabic and cellulose;
- of microbial origin such as xanthan gum natural agents, gellan gum, hyaluronic acid and dextran;
- animal origin, such as gelatin, collagen and chitosan natural agents;
- the mineral agents, such as clays and silicas and synthetic polymers such as polyacrylic and polyacrylamide agents.

The invention can be used in many areas such as for medicinal or cosmetic or coloring or dermatologic use or any combination of these areas. The following discussion of the invention based on possible areas of application shall not be construed as limiting as the basic idea is the same. The plants mentioned in connection with a specific application may also be utilized in connection with other applications. Two or more applications can be combined in a single product.

The product of the invention provides improved properties as regards at least one of substance concentration and substance release. Commonly known ways of administering a plant product can be improved and so far difficult ways for administering a plant product, e.g. sublingual administration, can be used more effectively.

The reason for this improvement is that due to the processing of the raw material(s) according to the invention a controlled amount of selected substances can be placed on the product, i.e. in the fibrous plant product or the plant extract. If desired one plant can substantially be reconstituted or reconstructed so that the final product comprises many or substantially all substances of the raw material. The reconstructed product is advantageous in comparison to the original plant, as the substances from the reconstructed product can be released in a controlled way, e.g. faster than from the natural plant. In addition, it may be desired to mix other substances from other plants or synthetical substances into the product to alter its mechanical or medicinal/dermatologic/cosmetic/coloring properties. Likewise it can be desired to separate certain undesired substances, e.g. pesticides, metals, or polyphenols.

The product according to the invention can also be designed to comprise different substances for different effects. In particular, the product can be designed to release different substances at different times and rates. In consequence, it is possible that a first substance provides a first effect and afterwards a second substance provides another effect. The times where the substances provide an effect can at least partially overlap. For example, it is possible to provide a dermatologic path which first provides a cooling effect and subsequently or overlapping releases a substance having a displeasing side effect such as burning or pricking. Likewise a medicinal product can comprise not only substances for providing a desired medicinal effect but also flavor or spice to make the administering more pleasant for children, adults or animals.

Medicinal Applications

According to one aspect, the invention can be used in medicinal applications. In particular, due to the improved properties of the product according to the invention the administering of medicinal substances becomes more efficient.

Sublingual administration of certain plant products was very often not possible as the concentration achieved was too low to obtain the desired medicinal effect. Having at least one of a higher concentration of the substance(s), a higher liberation rate of the substance(s), and better solubility properties makes sublingual administration of a plant product possible. Sublingual administration has certain advantages over oral administration. It is often faster and it ensures that the substance will risk degradation only by salivary enzymes before entering the bloodstream. Orally administered drugs must survive passage through the hostile environment of the gastrointestinal tract, which risks degrading and metabolizing them, either by stomach acid or bile, or by the many enzymes therein. Furthermore, after absorption from the gastrointestinal tract, such drugs must pass through the liver, where they may be extensively metabolized. Therefore, it is highly desirable to administer certain substances in a sublingual manner.

The product according to the invention can be used to prepare a bath such as a medicinal foot bath. For example, the product can be a powder or a paper like sheet. Also, the product can be a bag, optionally filled with conventional plant product and/or product according to the invention, e.g. small cut pieces. The product, e.g. in form of a bag, can be inserted into a solvent such as cold, warm or hot water to extract substances from the product. The solvent becomes enriched with substances released from the product and the enriched solvent can be used, e.g. as a medicinal foot bath. Similarly the solvent can be used for inhalation purposes. Similarly, the reconstituted plant product in form of a bag can be used for preparing other medicinal baths or liquids.

Plants for medicinal applications can be selected from one or more of *Achillea millefolium* L.; *Adhatoda vasica* Nees; *Aesculus hippocastanum* L.; *Agrimonia eupatoria* L.; *Agropyron repens* (L.); *Agropyron repens* (L.) P. Beauv.; *Allium sativum* L.; *Allium cepa* L.; *Aloe barbadensis* Miller; *Aloe ferox* Miller; *Althaea officinalis* L.; *Andrographis paniculata* Nees; *Angelica sinensis* (Oliv.) Diels; *Arctium lappa* L.; *Arctostaphylos uva-ursi* (L.) Spreng.; *Arnica montana* L.; *Artemisia absinthium* L.; *Avena sativa* L.; *Betula pendula* Roth; *Betula pubescens* Ehrh.; *Calendula officinalis* L.; *Camellia sinensis* (L.) Kuntze; *Capsella bursa-pastoris* (L.) Medikus; *Capsicum annuum* L. Heiser; *Carum carvi* L.; *Cassia senna* L.; *Cassia angustifolia* Vahl; *Centaurium erythraea* Rafn.; *Centella asiatica* L. Urban; *Cetraria islandica* (L.) Acharius s.l.; *Chamaemelum nobile* (L.) syn. *Anthemis nobilis* L.; *Chamaemelum nobile* (L.); *Anthemis nobilis* L.; *Chamomilla recutita* (L.) Rauschert; *Matricaria recutita* (L.); *Chelidonium majus* L.; *Cichorium intybus* L.; *Cimicifuga racemosa* (L.) Nutt.; *Cinnamomum verum* J. S. Presl; *Cinnamomum zeylanicum* Nees; *Citrus bergamia*

Risso; *Citrus bergamia* Risso & Poiteau.; *Citrus* spp.; *Cola nitida* (Vent.); *Cola acuminata* (P. Beauv.); *Cola acuminata* (P. Beauv.) Schott et Endl.; *Commiphora molmol* Engler; *Crataegus monogyna* Jacq. (Lindm.); *Crataegus laevigata* (Poir.) DC; *Cucurbita pepo* L.; *Curcuma longa* L.; *Cynara scolymus* L.; *Curcuma xanthorrhiza* Roxb.; *C. xanthorrhiza* D. Dietrich.; *Echinacea angustifolia* DC.; *Echinacea pallida* (Nutt.) Nutt.; *Echinacea purpurea* (L.) Moench.; *Eleutherococcus senticosus* (Rupr. et Maxim.) Maxim.; *Equisetum arvense* L.; *Erysimum officinale* L.; *Eschscholtzia california* Cham.; *Eucalyptus globulus* Labill.; *Eucalyptus polybractea* R. T. Baker; *Eucalyptus smithii* R. T. Baker.; *Euphrasia officinalis* L.; *Filipendula ulmaria* (L.) Maxim.; *Spiraea ulmaria* L.; *Foeniculum vulgare* Miller subsp. *vulgare* var. *vulgare*; *Fragaria vesca* L.; *Fraxinus excelsior* L.; *Fucus vesiculus* L.; *Fumaria officinalis* L.; *Gentiana lutea* L.; *Ginkgo biloba* L.; *Glycyrrhiza glabra* L.; *Glycyrrhiza inflata* Bat.; *Glycyrrhiza uralensis* Fisch.; *Grindelia robusta* Nutt.; *Grindelia squarrosa* (Pursh) Dunal; *Grindelia humilis* Hook. et Arn., Grindel; *Lavandula angustifolia* Mill.; *Lavendula officinalis* Chaix; *Leonurus cardiaca* L.; *Levisticum officinale* Koch.; *Linum usitatissimum* L.; *Marrubium vulgare* L.; *Matricaria recutita* L.; *Melaleuca alternifolia* (Maiden and Betche) Cheel; *Melilotus officinalis* (L.) Lam.; *Melissa officinalis* L.; *Mentha×piperita* L.; *Oenothera biennis* L.; *Oenothera lamarckiana* L.; *Olea europaea* L.; *Ononis spinosa* L.; *Ononis arvensis* L.; *Origanum dictamnus* L.; *Orthosiphon stamineus*; *Orthosiphon stamineus* Benth.; *Panax ginseng* C. A. Meyer.; *Passiflora incarnata* L.; *Paullinia cupana* Kunth; *Pelargonium sidoides* DC; *Pelargonium reniforme* Curt.; *Peumus boldus* Molina; *Phaseolus vulgaris* L.; *Picrorhiza kurroa* Royle ex. Benth.; *Pimpinella anisum* L.; *Plantago lanceolata* L.; *Plantago ovata* Forssk.; *Plantago afra* L.; *Plantago indica* L.; *Polypodium vulgare* L.; *Potentilla erecta* (L.) Raeusch.; *Primula veris* L.; *Primula elatior* (L.) Hill; *Prunus africana* (Hook f.) Kalkm.; *Quercus robur* L.; *Quercus petraea* (Matt.) Liebl.; *Quercus pubescens* Willd.; *Rhamnus purshianus* D.C.; *Rhamnus frangula* L.; *Rheum palmatum* L.; *Rheum officinale* Baillon; *Rhodiola rosea* L.; *Ribes nigrum* L.; *Rosa centifolia* L.; *Rosa gallica* L.; *Rosa damascena* Mill.; *Rosmarinus officinalis* L.; *Rubus idaeus* L.; *Ruscus aculeatus* L.; *Salix* [various species including *S. purpurea* L.; *S. daphnoides* Vill.; *S. fragilis* L.]; *Salvia officinalis* L.; *Sambucus nigra* L.; *Serenoa repens* (Bartram) Small; *Sabal serrulata* (Michaux) Nichols; *Silybum marianum* L. Gaertner; *Solanum dulcamara* L.; *Solidago virgaurea* L.; *Symphytum officinale* L.; *Syzygium aromaticum* (L.); *Syzygium aromaticum* (L.) Merill et L. M. Perry; *Tanacetum parthenium* (L.) Schultz Bip.; *Taraxacum officinale* Weber ex Wigg.; *Thymus vulgaris* L.; *Thymus zygis* Loefl. ex L.; *Tilia cordata* Miller; *Tilia platyphyllos* Scop.; *Tilia×vulgaris* Heyne; *Tilia tomentosa* Moench; *Trigonella foenum-graecum* L.; *Uncariae tomentosae* (Willd.) DC.; *Urtica dioica* L.; *Urtica urens* L.; *Vaccinium myrtillus* L.; *Valeriana officinalis* L.; *Verbascum thapsus* L.; *Verbascum densiflorum* Bertol.; *V. thapsiforme* Schrad; *Verbascum phlomoides* L.; *Viola tricolor* L.; *Viscum album* L.; *Vitex agnus-castus* L.; *Vitis vinifera* L.; *Zingiber officinalis* L.

As mentioned earlier, basically every plant having one or more desired substances for one or more of a medicinal or cosmetic or coloring or dermatologic application can be used as raw material for the product according to the invention.

Dermatologic Applications

Figure 2A:
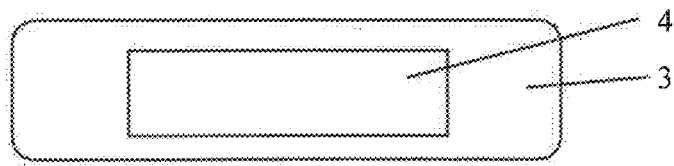
FIG. 2a is a schematic plan view of a patch of the invention.

Further, the product of the invention can be comprised by a dermatological or medical product. For example, a patch or mask as illustrated in FIG. 2a may comprise an adhesive area 3 and a pharmaceutically active area 4 comprising the product according to the invention. The patch can be applied to a skin to be treated, whereas the pharmaceutically active area 4 faces towards the skin to be treated. Once the patch is applied by pressing it against the skin to be treated, the adhesive area 3 secures the patch to the skin and the pharmaceutically active area 4 can unfold its effect. The patch or mask can have various shapes such as a preformed shape corresponding to a human face comprising openings, e.g. for nose, eyes, or mouth. A mask according to the invention may not comprise an adhesive area 3 to avoid irritation of the skin. Also, the mask may be rehydrated prior to use, e.g. by applying cold or warm water or other liquids or solvents or mixture of them. In this way release of the substances contained in the pharmaceutically active area 4 can be improved. Also, the adhesive area 3 and the pharmaceutically active area can at least partially or substantially entirely overlap. Also, the adhesive area 3 can be omitted in case it is not necessary or in case the pharmaceutically active area 4 comprises substances with an adhesive main or side effect.

Figure 2B:
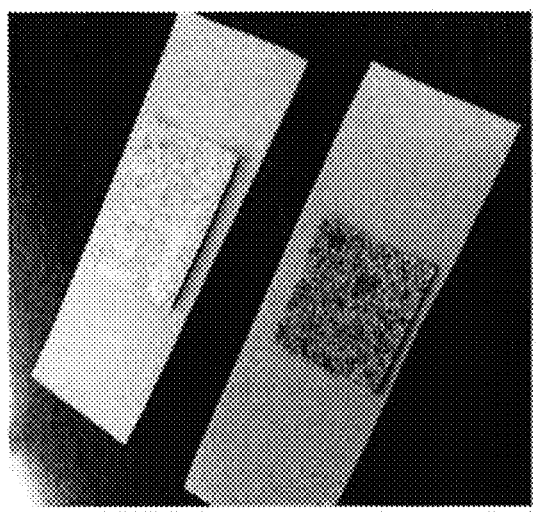
FIG. 2b is an illustration of a wound dressing application of the invention.

FIG. 2b illustrates an exemplary patch wherein the active area is formed by reconstituted tea (sample 1562A1), which was laminated with a 16-gsm synthetic (Rayon fibers) film on one side.

One or both of the plant extract and the fibrous plant product, in particular the substances contained therein, are able to act on the skin, for example by diffusion or penetration into the skin, or simply by the effect of surface contact with skin. One or more of the following substances can be used: chamomile, wild pansy, *aloe* vera, tea tree, St. John's Wort, burdock, witch hazel, willow, dandelion, or oregano. With regard to further exemplary plants for dermatologic applications reference is made to the following literature, which is incorporated herein by reference in its entirety:

ESCOP Monographs, 3 books, Ed. Thieme ISBN 978-1-901964-08-0; and

Barnes J., Anderson A. L., Phillipson D. 2007. Herbal Medicines, Ed. Pharmaceutical Press, 710 pages, ISBN 978 0 85369 623 0.

Figure 1B:
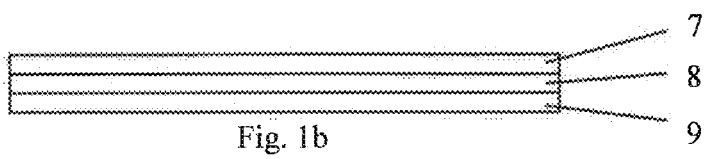
FIG. 1b is a schematic cross sectional view of an exemplary multilayer product of the invention.
Figure 1C:
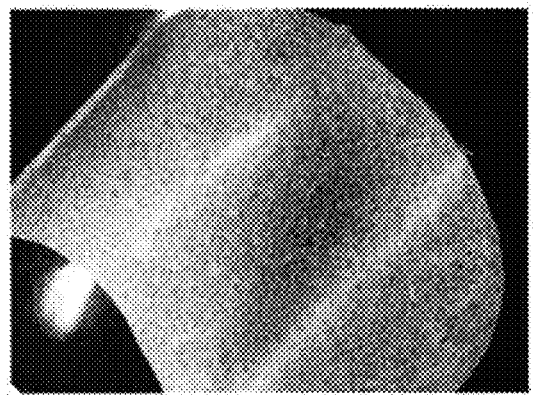
FIG. 1c is an illustration of an exemplary multilayer facial mask of the invention.

An exemplary multilayer facial mask is illustrated in FIGS. 1b and 1c. Layer 8 comprises reconstituted material with a fibrous plant product and a plant extract. Layer 9 is a lower layer which comes into contact with the skin and comprises cellulosic fibers, e.g. abaca, which may offer a soft and white surface. Layer 9 may have a weight from 10 gsm to 100 gsm. Preferably layer 9 is porous enough to let plant extract reach the skin. Layer 9 may also contain a hydrophobic or hydrophilic solution (such as water or humectants or alcohols or a blend of them) in order to facilitate plant extract diffusion. The same solution can also contain one or more ingredients such as extracts, scents, coloring agents, preserving agents, emulsifiers, lubricants, acid and/or base to adjust pH. Layer 7 is an upper (outside) layer comprising synthetic fibers, such as polyamide, polyethylene, polypropylene, rayon such as Viscose/Tencel and polyester and blends of thereof. Layer 7 may have a weight from 10 gsm to 500 gsm depending on product applications. Layer 7 may provide appropriate physical characteristics to the end product.

A mask according to the invention may comprise different zones comprising different active substances, e.g. for forhead and cheeks region a first substance or mix of substances, for eye region a second substance or mix of substances and for nose region a third substance or mix of substances.

US patent application US 2009/0280150 A1 (issued on Dec. 3, 2013 as U.S. Pat. No. 8,597,667 B2), which is incorporated herein by reference, discloses a cosmetic facial mask for targeted and simultaneous treatment of multiple skin conditions (see, e.g. paragraph 27). The mask is described as a flexible substrate being shaped to fit facial features, having openings for eyes, nose and mouth (see, e.g., paragraphs 10 and 28). The substrate includes at least two isolated, discrete regions imprinted with a different skin benefit agent for releasable delivery (see, e.g. paragraph 5). The reconstituted plant material of the present invention can be provided or used in a similar way, i.e., in the form of or as part of a material having discrete regions providing one or more active agents delivered from reconstituted plant material, as described, for example, in connection with cosmetic sheets and the targeted delivery of a skin benefit agent in paragraphs 5 and 10 as well as in facial masks as discussed in paragraphs 26 to 33 in combination with FIGS. 1 to 6 of US patent application US 2009/0280150 A1.

Further exemplary plants for medicinal applications can be selected from one or more of *Abies* spp.; *Achillea officinalis*; *Aesculus hippocastanum*; *Agrimonia eupatoria*; *Aloe* spp.; *Althaea officinalis*; *Anthemis nobilis*; *Arctium majus*; *Arnica montana*; *Balsamita major*; *Brassica* spp.; *Calendula officinalis*; *Capsella bursa pastoris*; *Centaurea cyanus*; *Centella asiatica*; *Cinchona* spp.; *Cochlearia armoracia*; *Commiphora* spp.; *Corylus avelana*; *Crocus sativus*; *Cupressus sempervirens*; *Erysimum* spp.; *Eucalyptus* spp.; *Ficaria ranunculoides*; *Filipendula ulmaria*; *Fucus vesiculosus*; *Ginkgo biloba*; *Glycyrrhiza* spp.; *Hamamelis virginiana*; *Hedera helix*; *Hypericum perforatum*; *Juglans regia*; *Krameria tetrandra*; *Lamium* spp.; *Lavandula* spp.; *Lippia citriodora*; *Malva sylvestris*; *Matricaria recutita*; *Melaleuca* spp.; *Melilotus officinalis*; *Mentha* spp.; *Nuphar luteum*; *Origanum majorana*; *Paullinia cupana*; *Petroselinum crispum*; *Pinus* spp.; *Plantago* spp.; *Polygonum bistorta*; *Populus* spp.; *Potentilla erecta*; *Quercus* spp.; *Raphanus sativus*; *Rheum officinale*; *Ribes nigrum*; *Rosa* spp.; *Rubus* spp.; *Ruscus aculeatus*; *Salicaria officinalis*; *Salix* spp.; *Salvia* spp.; *Satureia montana*; *Symphytum officinale*; *Syzygium aromaticum*; *Thea sinensis*; *Thea* spp.; *Thymus* spp.; *Tilia* spp.; *Tropaeolum majus*; *Vaccinium myrtillus*; *Verbascum thapsiforme*; *Verbena officinalis*; *Viburnum* spp.; *Viola* spp.; *Vitis vinifera*; *Ziziphus jujuba*.

As mentioned earlier, basically every plant having one or more desired substances for one or more of a medicinal or cosmetic or coloring or dermatologic application can be used as raw material for the product according to the invention.

Preferred substances in the product according to the invention are selected from one or more of antioxidant agent, anti-radical agent, a depigmenting agent, a liporegulating agent, an anti-acne agent, an antiseborrhoeic agent, an anti-aging agent, a softener, an anti-wrinkle agent, an anti-inflammatory agent, a healing agent, a hydrating agent, an antibacterial agent, an antifungal agent, a vitamin, a protein, an amino acid, a fatty oil, an essential oil agent, a phytosterol, a ceramide, a clay and a UV filter.

Cosmetic Applications

The product according to the invention may also be used in cosmetic applications. A cosmetic mask may correspond to the mask as explained in the context of dermatologic applications but comprising substances with a cosmetic effect rather than substances with a medicinal and/or dermatologic effect. As already mentioned, also combinations are possible, e.g. a mask comprising at least one of a cosmetic, dermatologic and medicinal effect. Similarly, the bag as discussed in connection with a medicinal footbath application can also be used in cosmetic and/or coloring applications.

Just like with other applications it is also in cosmetic applications desirable to not only control the amount of desired substances but also to remove selectively undesired substances like pesticides, metals, polyphenols or sensitizing agents. Indeed, it has been proved that molecules like polyphenols can damage hair or skin.

According to the invention it is possible to alter the properties of the resulting product by adding further excipients like extracts, scents, coloring agents, preserving agents, emulsifiers, lubricants or acid or base to adjust pH.

Plants for cosmetic applications can be selected from one or more of *Achillea millefolium*; *Actinidia chinensis*; *Aesculus hippocastanum*; *Agrimonia eupatoria*; *Agropyrum repens*; *Aloe* spp.; *Althaea* spp.; *Amyris balsamifera*; *Ananas sativus*; *Anethum graveolens*; *Angelica archangelica*; *Arctium majus*; *Arctostaphyllos uva ursi*; *Arnica montana*; *Artemisia* spp.; *Bambusa arundinacea*; *Artocarpus heterophyllus*; *Ascophyllum nodosum*; *Asparagus officinalis*; *Avena sativa*; *Bambusa arundinacea*; *Bandeiraea simplicifolia*; *Bergenia crassifolia*; *Betula* spp.; *Boerhavia diffusa*; *Boswellia carteri*; *Brassica* spp.; *Broussonetia papyrifera*; *Calendula officinalis*; *Calluna vulgaris*; *Camellia* spp.; *Cananga odorata*; *Capsicum* spp.; *Carapa guaianensis*; *Carica papaya*; *Carum carvi*; *Cassia* spp.; *Castanea* spp.; *Centaurea cyanus*; *Centella asiatica*; *Chamomilla* spp.; *Chenopodium quinoa*; *Chondrus crispus*; *Chrysanthellum indicum*; *Chrysanthemum cinerariaefolium*; *Cichorium intybus*; *Cinchona* spp.; *Cinnamomum* spp.; *Cistus labdaniferus*; *Citrullus* spp.; *Citrus* spp.; *Cnicus benedictus*; *Cochlearia officinalis*; *Coffea* spp.; *Commiphora abyssinica*; *Coriandrum sativum*; *Corylus avelana*; *Crithmum maritimum*; *Crocus* spp.; *Cucumis sativus*; *Cucurbita* spp.; *Cupressus sempervirens*; *Curculigo orchioides*; *Curcuma* spp.; *Cyathea medullaris*; *Cydonia vulgaris*; *Cymbopogon* spp.; *Cynara scolymus*; *Daucus carota*; *Dioscorea* spp.; *Drosera* spp.; *Echinacea* spp.; *Eclipta prostrata*; *Epilobium angustifolium*; *Equisetum arvense*; *Erica cinerea*; *Euonymus europaeus*; *Euphorbia* spp.; *Euphrasia officinalis*; *Filipendula ulmaria*; *Foeniculum* spp.; *Fragaria* spp.; *Fraxinus* spp.; *Fucus* spp.; *Fumaria officinalis*; *Garcinia cambodgia*; *Gaultheria procumbens*; *Geranium robertianum*; *Ginkgo biloba*; *Glycine soja*; *Glycyrrhiza glabra*; *Gossypium* sp.; *Grindelia* spp.; *Haematoxylum campechianum*; *Hamamelis virginiana*; *Harpagophytum procumbens*; *Hedera helix*; *Helianthus annuus*; *Helichrysum italicum*; *Hibiscus sabdariffa*; *Hieracium pilosella*; *Himanthalia elongata*; *Humulus lupulus*; *Hypericum perforatum*; *Hyssopus officinalis*; *Ilex* spp.; *Ipomoea* spp.; *Iris* spp.; *Jasminum* spp.; *Juniperus* spp.; *Krameria triandra*; *Larix decidua*; *Laminaria* spp.; *Lamium* spp.; *Larrea divaritica*; *Laurus nobilis*; *Lavandula* spp.; *Lithothamnium calcareum*; *Lythrum salicaria*; *Mangifera indica*; *Marrubium vulgare*; *Marsdenia condurango*; *Melaleuca* spp.; *Melilotus officinalis*; *Melissa officinalis*; *Mentha* spp.; *Mucuna pruriens*; *Musa* spp.; *Myrtus communis*; *Myrica cerifera*; *Nasturtium officinalis*; *Nelumbo nucifera*; *Nephelium longana*; *Nicotiana* spp.; *Nigella sativa*; *Nuphar* spp.; *Ocimum basilicum*; *Olea curopaea*; *Opuntia* spp.; *Orchis mascula*; *Origanum* spp.; *Oryza* spp.; *Palmaria palmata*; *Panax ginseng*; *Papaver rhoeas*; *Paullinia cupana*; *Persea* spp.; *Petroselinum* spp.; *Phaseolus* spp.; *Pimenta* spp.; *Pinus* spp.; *Plantago* spp.; *Plectranthus barbatus*; *Polygala* spp.; *Polygonum* spp.; *Populus nigra; Porphyra umbilicalis; Portulaca oleracea; Potentilla* spp.; *Primula* spp.; *Prunus* spp.; *Punica granatum; Pygeum africanum; Pyrus malus; Quassia amara; Quercus* spp.; *Quillaja saponaria; Ranunculus ficaria; Raphanus* spp.; *Rhaponticum* spp.; *Ravensana aromatica; Rheum* spp.; *Rhodiola rosea; Ribes nigrum; Rosa* spp.; *Rosmarinus officinalis; Rubia tinctorium; Rubus* spp.; *Rumex occidentalis; Ruscus aculeatus; Saccharum officinarum; Satureia montana; Salix alba; Salvia* spp.; *Sambucus nigra; Schinus molle; Senna* spp.; *Serenoa repens; Silybum marianum; Solanum* spp.; *Solidago* spp.; *Sophora japonica; Sterculia* spp.; *Symphytium officinale; Syzygium aromaticum; Tagetes* spp.; *Tamarindus indica; Tanacetum* spp.; *Thea sinensis; Theobroma* spp.; *Thymus* spp.; *Tilia* spp.; *Trigonella foenum graecum; Triticum vulgare; Tropaeolum* spp.; *Tussilago farfara; Undaria* spp.; *Urtica dioica; Usnea* spp.; *Valeriana officinalis; Verbascum* spp.; *Verbena officinalis; Veronica* spp.; *Viola odorata; Viburnum* spp.; *Vinca minor; Vitis vinifera; Zea mays; Zingiber officinale.*

As mentioned earlier, basically every plant having one or more desired substances for one or more of a medicinal or cosmetic or coloring or dermatologic application can be used as raw material for the product according to the invention.

Coloring Applications

The product according to the invention can be used in applications of coloring such as coloring of one or more of hair, skin and items like cloths or bags or food. The term coloring shall encompass all coloring treatments, such as tinting, dyeing, highlighting and bleaching. A coloring product according to the invention can comprise a mask as discussed in connection with dermatologic applications, the mask comprising coloring substance(s). The product of the invention enables a more efficient coloration in the sense that more coloring agents can be released from the reconstituted plant than from a natural plant for a given weight of material in the same time. Also, the product of the invention enables faster coloration than with the same non reconstituted plant because the extraction or liberation is faster than the natural plant. Indeed, coloring agents can be applied onto the surface of the product by the process as explained later on and can be released as soon as they get in touch with a solvent, such as water. Coloring agents can be soluble. Solubles or coloring agents can be precisely measured and their amount can be precisely adjusted (decreased, at standard level, or increased), so it allows a better control. Moreover, the product can comprise always substantially the same quantity of substance(s), i.e. from one production to another. Therefore, variations of the coloring effect can be reduced or avoided. This is equally true for all other applications, i.e. medicinal, cosmetic and dermatologic applications.

For coloring matters it is possible to blend various plants, herbs, medicinal plants, tea, vegetables dye plants and spices to obtain a specific color. For example, if it is desired to color light hair into dark hair, a blend of henna and indigo may be used.

The invention also relates to a product for coloring items such as fabric or leather or textiles or food or other items which can be colored with a substance comprised by a plant product.

Preferred plants for cosmetic or coloring applications are one or more from the group comprising: *Indigofera Tinctoria, Lawsonia Inermis, Curcuma Longa, Juglans Regia, Rubia Tinctorum, Quillaja Saponaria, Chamaemelum Nobile.*

The following provides some exemplary applications with the respective plant:
Colorant: *Haematoxylum Campechianum, Lawsonia Inermis, Bixa Orellana;*
Hair-Lightning: *Camomile;*
Firming up: *Sphenophyta;*
Hydrating: *Fucus, Althaea officinalis, Camomile.*

In the products of the invention, the plant is for example selected from the group consisting of herbs, medicinal plants, tea, vegetables dye plants and spices, including mixtures thereof.

Exemplary plants for cosmetic applications are the following:
Red/Brown: *Asperula tinctoria; Carthamus tinctorius; Camellia* spp.; *Galium odoratum; Lawsonia inermis; Phytolacca decandra; Pinus sylvestris; Polygonum aviculare; Pterocarpus santalinus; Rhamnus alaternus; Rubia tinctoria* and *Rubia* spp.; *Trigonella foenum-graecum;*
Black/Dark: *Acacia catechu; Juglans regia; Quercus infectoria; Quercus* spp.; *Terminalia* spp.; *Uncaria gambier;*
Red/Purple: *Alkanna tinctoria; Beta vulgaris; Caesalpinia brasiliensis; Caesalpinia sappan; Capsicum annuum; Daucus carota; Fucus* spp.; *Morus nigra; Papaver rhoeas; Punica granatum; Ribes nigrum; Rubus fruticosus; Rocella tinctoria* or *Oricella; Salix purpurea; Sambucus nigra; Vaccinium macrocarpon; Vaccinium* spp.; *Vitis vinifera;*
Yellow/Orange: *Anthemis tinctoria; Arbutus unedo; Bixa orellana; Carthamus tinctorius; Cinnamomum* spp.; *Curcuma* spp.; *Crocus sativus; Galeopsis tetrahit; Genista tinctoria; Hypericum perforatum; Matricaria* spp.; *Memecyton tinctorius; Morus tinctoria; Punica granatum; Quercus tinctorius; Quercus velutina; Reseda luteola; Rheum palmatum; Solidago virgaurea; Sophora japonica; Spirea aruncus; Tagetes patula; Tanacetum vulgare; Tussilago farfara;*
Green: *Allium porum; Berberis vulgaris; Gladiatus communis; Ligustrum vulgare; Rhamnus cathartica; Solanum nigrum; Spinacia oleracea;*
Blue: *Baptisia tinctoria; Centaurea cyanus; Chrozophora tinctoria; Hematoxylum campechianum; Indigofera* spp.; *Isatis tinctoria; Lonchocarpus cyanescens; Mahonia multiflorum; Marsdenia tinctoria; Nerium tinctorium; Ocriolaria ocrina; Polygonum tinctorium; Wrightia tinctoria.*

As mentioned earlier, basically every plant having one or more desired substances for one or more of a medicinal or cosmetic or coloring or dermatologic application can be used as raw material for the product according to the invention.

Exemplary Applications

In the following exemplary applications with corresponding plants are provided. As already mentioned earlier, the respective applications can also comprise more plants and plants mentioned in connection with an application may also be used in other applications. Also, two or more plants with different effects may be used together in a product according to the invention.
Plants which may be used as an antiseptic: *Cinnamomum camphora, Lavendula* spp.
Plant which may be used as a bactericidal: *Camellia* spp.
Plant which may be used for skin cleaning, foaming: *Hedera helix*

Plants which may be used as a deodorant: *Cucumis sativus, Symphytum officinalis*

Plant which may be used as a repellent: *Cymbopogon winterianus*

Plants which may be used for soothing: *Aloe* spp., *Symphytum officinalis, Ranunculus ficaria, Glycyrrhiza glabra*

Plants which may be used as a decongestant: *Arnica montana, Calendula officinalis*

Plant which may be used as against red blotches: *Calendula officinalis*

Plants which may be used for relaxing: *Lavendula* spp., *Thymus* spp.

Plants which may be used as an anti-inflammatory: *Aloe* spp., *Laminaria* spp.

Plants which may be used as a phlebotonic: *Aesculus hippocastanum, Sophora japonica, Vitis vinifera*

Plants which may be used as an emollient: *Cucumis sativus, Symphytum officinalis*

Plants which may be used as an astringent: *Haematoxylum campechianum, Salvia* spp.

Plants which may be used for stimulating/toning: *Panax ginseng, Echinacae* spp.

Plant which may be used for firming up: *Equisetum arvense*

Plant which may be used for restructuring: *Coffea* spp.

Plants which may be used for revitalizing: *Fucus* spp., *Laminaria* spp.

Plants which may be used as an antioxidant: *Camellia* spp., *Thymus* spp., *Origanus* spp.

Plants which may be used for hydrating: *Fucus* spp., *Althaea* spp.

Plants which may be used for slimming: *Coffea* spp., *Fucus* spp., *Equisetum arvense*

Plants which may be used for refreshing: *Cucumis sativus, Mentha* spp.

Plant which may be used for depigmenting: *Achillea millefolium*

Plants which may be used for capillary fragility and venous problems:

*Aesculus hippocastanum, Agrimonia eupatoria, Arnica montana. Capsella bursa pastoris, Centella asiatica, Coryllus avelana, Cupressus sempervirens, Ficaria ranunculoides, Ginkgo biloba, Hamamelis virginiana, Krameria tetrandra, Melilotus officinalis, Polygonum bistorta, Potentilla erecta, Quercus* spp., *Ribes nigrum, Ruscus aculeatus, Salicaria officinalis, Vaccinium myrtillus, Viburnum* spp., *Vitis vinifera.*

Plants which may be used to clean dermal sores and wounds:

*Calendula officinalis, Commiphora* spp., *Lavandula* spp., *Satureia montana, Syzygium aromaticum, Salvia* spp., *Thymus* spp.

Plants which may be used against scalp itch and dandruff:

*Cinchona* spp., *Eucalyptus* spp., *Juglans regia, Lamium* spp., *Mentha* spp., *Salvia* spp., *Tropaeolum majus.*

Plants which may be used to soothe skin in case of surface cracks, dryness, insect bites, abrasions, burns and diaper rash:

*Achillea officinalis, Aloe* spp., *Althaea officinalis, Anthemis nobilis, Arctium majus, Balsamita major, Centaurea cyanus, Centella asiatica, Hedera helix, Hypericum perforatum, Lippia citriodora, Malva sylvestris, Matricaria recutita, Mentha* spp., *Nuphar luteum, Origanum majorana, Petroselinum crispum, Plantago* spp., *Populus* spp., *Raphanus sativus, Rosa* spp., *Symphytum officinale, Thea sinensis, Tilia* spp., *Verbascum thapsiforme, Viola* spp.

Plants which may be used in case of teething:

*Aloe* spp., *Crocus sativus, Filipendula ulmaria, Rheum officinale, Salix* spp., *Syzygium aromaticum.*

Plants which may be used to lose weight:

*Hedera helix, Fucus vesiculosus, Paullinia cupana, Thea* spp.

Plants which may be used in case of eye irritation:

*Anthemis nobilis, Centaurea cyanus, Hamamelis virginiana, Matricaria recutita, Melilotus officinalis, Plantago* spp., *Verbena officinalis.*

Plants which may be used in case of bronchial disorders, coughs, colds:

*Abies* spp., *Brassica* spp., *Eucalyptus* spp., *Melaleuca* spp., *Pinus* spp., *Populus* spp.

Plants which may be used for oral applications:

*Althaea officinalis, Anthemis nobilis, Cochlearia armoracia, Erysimum* spp., *Glycyrrhiza* spp., *Malva sylvestris, Mentha* spp., *Pinus* spp., *Rubus* spp., *Salicaria officinalis, Ziziphus jujuba.*

Method

The invention further relates to a method for producing the product. For example, the method comprises the steps of:
a) extracting one or more substances of at least one plant to obtain a plant extract;
b) separating the plant extract from the at least partially fibrous residue;
c) optionally refining the residue;
d) preparing a sheet like product from the residue, optionally a sheet like product;
c) optionally concentrating or purifying or aromatizing the plant extract;
f) applying the plant extract of step b) or e) to the sheet of step d); and
g) optionally drying the product of step f)

In one embodiment of the invention, one or more plant components (plant material or plant funish) such as, for example, stems, scraps, leaves, fines, dust and/or shorts, are initially mixed with a solvent (e.g., water and/or other compounds) at elevated temperatures. For example, various solvents that are water-miscible, such as alcohols (e.g., ethanol), can be combined with water to form an aqueous solvent. The water content of the aqueous solvent can, in some instances, be greater than 50% by weight of the solvent. In one embodiment, the water content is at least about 70%, or at least about 80%, or at least about 90% or about 100% by weight of the solvent. Deionized water, distilled water or tap water may be employed. The amount of the solvent in the suspension can vary widely, but is generally added in an amount from about 75% to about 99% by weight of the suspension. However, the amount of solvent can vary with the nature of the solvent, the temperature at which the extraction is to be carried out, and the type of plant components.

After forming the solvent/plant furnish mixture, some or all of a soluble extracts fraction of the furnish mixture may be optionally separated (e.g., extracted) from the mixture. If desired, the aqueous solvent/plant furnish mixture can be agitated during extraction by stirring, shaking or otherwise mixing the mixture in order to increase the rate of extraction. Typically, extraction is carried out for about 0.5 hours to about 6 hours. Moreover, although not required, typical extraction temperatures range from about 10° C. to about 100° C.

Prior to the extraction step an optional grinding or cutting step can be used, in order to shred the plant or plant part and thus to break the plant's cell walls.

Once separated from the insoluble residue fraction of the plant solution, the soluble extracts fraction can optionally be concentrated using any known type of concentrator, such as a vacuum evaporator. In one embodiment, the soluble component may be highly concentrated. Moreover, the concentrated or unconcentrated soluble extracts fraction can be utilized in any manner desired. For example, the soluble extracts fraction can be utilized as a flavoring material or a portion can be added to the insoluble residue fraction.

Once extracted, the insoluble residue fraction can optionally be subjected to one or more mechanical refiners to produce a fibrous pulp. Some examples of suitable refiners can include disc refiners, conical refiners, and the like. The insoluble residue fraction can be utilized in any manner desired. For example, the insoluble residue fraction can be used as a flavoring material, used to produce a composition of the invention, which is herein also referred to as reconstituted plant material.

To produce a product of the invention, the insoluble residue fraction can be transferred to a papermaking station. The papermaking station includes a forming apparatus, which may include, for example, a forming wire, gravity drain, suction drain, felt press, Yankee dryer, drum dryers, etc. In general, the insoluble residue fraction may be in the form of a pulp. In the forming apparatus, the pulp is laid onto a wire belt forming a sheet-like shape. Excess water is removed from the sheet using gravity drains, suction drains, presses, and dryers. Thereafter, if desired, a portion of the soluble extracts fraction may be reapplied to the insoluble residue fraction. When the insoluble residue fraction is recombined with the soluble extracts fraction, the resulting plant product is generally referred to as "reconstituted plant material".

Reconstituted plant material can generally be formed in a variety of ways. For instance, in one embodiment, band casting can be utilized to form the reconstituted plant material. Band casting typically employs a slurry of finely divided plant parts mixed with a binder such as gum arabic, guar gum, alginate, xanthan, cellulose and cellulose derivatives (such as carboxy methyl cellulose (CMC), hydroxypropyl methyl cellulose (HPMC)), pectines or starch that is coated onto a steel band and then dried. In one embodiment, the method is performed according to a process similar to the conventional tobacco reconstitution process, which is for example described in U.S. Pat. Nos. 3,353,541; 3,420,241; 3,386,449; 3,760,815; and 4,674,519; which are incorporated herein in their entirety by reference thereto. The method for producing the products of the invention can also be performed by a papermaking process, in order to reconstitute any plant components (such as stems, scraps, leaves, fines, dust and/or shorts) into a paper-like product. Some examples of such processes are described in U.S. Pat. Nos. 3,428,053; 3,415,253; 3,561,451; 3,467,109; 3,483,874; 3,860,012; 3,847,164; 4,182,349; 5,715,844; 5,724,998; and 5,765,570; which are also incorporated herein in their entirety by reference thereto for all purposes. For example, the formation of the products of the invention using papermaking techniques can involve the steps of mixing herbs, medicinal plants, tea, vegetables dye plants and/or spices with water, extracting the soluble ingredients therefrom, concentrating the soluble ingredients, refining the herbs, medicinal plants, tea, vegetables dye plants and/or spices, forming a web, reapplying the concentrated soluble ingredients, drying, and threshing.

Once extracted, the insoluble, solids portion can optionally be subjected to one or more mechanical refiners to produce a fibrous pulp. Some examples of suitable refiners can include disc refiners, conical refiners, and the like, well known to a skilled person. The pulp from the refiner can then be transferred to a papermaking station that includes a forming apparatus, which may include, for example, a forming wire, gravity drain, suction drain, felt press, Yankee dryer, drum dryers, etc. In such a forming apparatus, the pulp is laid onto a wire belt forming a sheet-like shape and excess water is removed by the gravity drain and suction drain and presses. Once separated from the insoluble portion of the plant solution (plant extract), the soluble portion can optionally be concentrated using any known type of concentrator, such as a vacuum evaporator.

One or more wet strength agents may be added preferably to the fibrous portion in order to reduce potential degradation of the reconstituted material when it is brought into contact with a liquid (e.g. water), such as upon infusion in water. Any suitable wet strength agent preferably selected for food, medicinal, cosmetic, coloring or dermatologic applications may be used such as polyamide-epichlorohydrin resins, polyamine-epichlorohydrin resins, poly(aminoamide)-epichlorohydrin resins, urea-formaldehyde resins, melamine-formaldehyde resins, alkyl ketene dimer, alkyl succinic anhydride, polyvinylamines, oxidized polysaccharides (such as oxidatively degraded starch), glyoxalated polyacrylamide resins, polyimines such as polyethyleneimine. Wet strength agents are well known to the skilled person and described in Ingredients Standards, such as BFR (Bundesinstitut für Risikobewertung) XXXVI and BFR XXXVI/1 or FDA (Food & Drug Administration) 21 CFR 176.170, FDA 21 CFR 176.110, FDA 21 CFR 176.120, FDA 21 CFR 176.1180. The wet strength agent is for example used in an amount of about 0.1% w/w to about 20% w/w, preferably of about 1% w/w to about 10% w/w, more preferably of about 5% w/w. The wet strength agent is preferably added to the fibrous portion when or before making the sheet-like product (see step d) above).

In one embodiment, the water used for extraction is hot water, preferably of about 30° C. to 100° C., about 40° C. to 90° C., or about 50° C. to 80° C., or more preferably of about 70° C.

In one embodiment, the coating ratio of solubles portion onto the fiber web is about 5% to 80% (w/w), about 10% to 70% (w/w), or more preferably between about 20% and 50% (w/w). In some embodiments, the coating ratio or soluble portion that is added back to the base web (fiber web) is similar to the portion of soluble material contained in and extracted from the original plant (so called "standard level").

In one embodiment, the base weight of the final product is about 20 to about 200 g/m$^2$ (dry basis), more preferably about 90 g/m$^2$ to about 120 g/m$^2$.

The extraction time depends on the herbs, medicinal plants, tea, vegetables dye plants and/or spices subjected to the extraction process. In one embodiment of the invention, the extraction time is about 15 to 60 minutes, preferably 45 minutes.

In one embodiment of the method of the invention, the extracting step is performed using components of a blend of plants, in another embodiment, extracting step is performed using components of a single plant.

Extraction may also be performed by means other than using hot water, namely by extraction with supercritical gases, such as carbon dioxide, or by using, for example, ethanol, hexane, acetone, R134a (1,1,1,2-tetrafluoroethane), carbon dioxide and hydrofluorocarbons. In one embodiment, the extraction can be carried out by using at least one solvent at room temperature and under atmospheric pressure. Extraction may also be performed by using a mixture of different solvents. In another embodiment, extraction may be performed using at least one solvent, such as for example R134a or carbon dioxide, at different temperatures and at different pressures and different states (liquid or gaseous). For example, extraction may be performed using solvents in a liquid state (such as solvent that are volatile or non-volatile at room temperature), in a subcritical state (such as water at a temperature above 100° C. and a pressure above 1 bar), or in a supercritical state (such as carbon dioxide at a temperature above 31° C. and a pressure above 73 bar).

Certain plants may require specific extraction conditions (time, temperature, solid/liquid ratio) due to the ingredients contained therein, which may be temperature sensitive or must not be subjected to certain extraction conditions. For example, extraction of lycopene from tomatoes must be performed by using specific enzymes to liberate the product from tomatoes cells. In connection with the present invention, processing aids may be used to improve extraction, such as pH modifiers (such as, for example, NaOH or organic acids), microwaves, pressure, ultrasound, enzymes such as for example proteases, amylases, cellulose, and/or pectinases. Whenever reference is made herein to "extraction", the term includes the aforementioned alternative extraction means. The extraction used in connection with the present invention can be performed in a continuous or discontinuous matter. The extraction conditions are well known to the skilled artisan and described in standard text books, such as Handbook of Separation Techniques for Chemical Engineers, Third Edition (March 1997), Philip A. Schweitzer, McGraw-Hill Inc.

In one embodiment, the extraction and/or pressing may be performed using at least a portion of the plant material, fresh, frozen or dried, selected from one or more of root, stem, trunk, caulis, leaf, lamina, fruit, flower, seed or bark.

Separation of the soluble portion (plant extract) from the non-soluble portion (solid plant particles) can be performed by separating the liquid phase from the solid phase, such as by filtration, with or without pressure, by centrifugation or other methods commonly used in the laboratory and well-known to the skilled person.

In one embodiment of the method where a mixture or blend of plants is used, the non-soluble portion of the plant is mixed with the non-soluble portion of at least one further plant prior to preparing the sheet.

Certain embodiments of the method of the invention use the soluble portion of step b) or concentrated soluble portion of step e), which is mixed with the soluble portion or concentrated soluble portion of at least one further plant prior to applying the soluble portion or concentrated soluble portion to the sheet.

For certain applications it is desirable to adjust the composition by adding or removing ingredients or components to or from the plant extract and/or the non-soluble plant particles prior to producing the final product of the invention. Such adjustment may be performed to modify/improve chemical, physical and/or sensory characteristics of the finished product. The invention thus encompasses methods, further comprising the step of adding or removing ingredients from the soluble portion (plant extract) and/or from the non-soluble portion (solid plant particles) prior to applying the soluble portion of step b) or concentrated soluble portion of step e) to the sheet of step d).

In some embodiments, the sheet or sheet-like product which is obtained in step g) is a web or fiber-web. The sheet-like product or web may be used in different sizes and shapes. In some cases, the composition of step g) is further cut or broken into small regularly or irregularly shaped forms or processed to obtain a powder, e.g. by grinding. In addition to cutting or breaking the sheet or fibrous web to a desired size and/or shape, it may be dried to the desired final moisture content.

One possible grinding method is cryogenic grinding. Cryogenic grinding, also known as freezer milling, freezer grinding, or cryomilling, is the act of cooling or chilling a material and then reducing it into a small particle size. Heat and oxidation reactions usually occur on the material with standard grinding technologies, at room temperature. Thanks to cryogenic grinding, enzymes, vitamins and many other active molecules are preserved from such reactions. This technology is used to prepare medicinal plant powders.

The product according to the invention may also be pelletized, e.g. to produce tablets or granule. Pelletizing is the process of compressing or molding a material into the shape of a pellet. Ingredients are normally first hammered to reduce the particle size of the ingredients. Ingredients are then batched, and then combined and mixed thoroughly by a feed mixer. Once the feed has been prepared to this stage the feed is ready to be pelletized. Pelletizing is done in a pellet mill, where feed is normally conditioned and thermally treated in the fitted conditioners of a pellet mill. The feed is then pushed through the holes and a pellet die and exit the pellet mill as pelleted feed. After pelleting the pellets are cooled with a cooler to bring the temperature of the feed down. Other post pelleting applications include post-pelleting conditioning, sorting via a screen and maybe coating if required.

In accordance with the present invention the plant is selected from the group consisting of herbs, medicinal plants, tea, vegetables dye plants and spices, including mixtures thereof. Exemplary plants that are useful in accordance with the present invention have already been discussed earlier in connection with certain applications.

In a further embodiment, the invention relates to a fiber-web comprising from about 5% to about 100% (w/w), preferably at least about 10%, at least about 20%, at least about 30%, at least about 40%, at least about 50%, at least about 60%, at least about 70%, at least about 80%, at least about 90%, or about 100%, fibers of herbs, medicinal plants, tea, vegetables dye plants and/or spices. In one embodiment, the fiber-web further comprises cellulosic and/or synthetic fibers, and fibers of herbs, medicinal plants, tea, vegetables dye plants and/or spices in a ratio of for example: 40/60 (w/w), 50/50 (w/w), 60/40 (w/w), 70/30 (w/w) or 20/80 (w/w). In another embodiment of the invention, the fiber-web of the present invention is obtainable by the method disclosed herein, namely as an intermediate product in step d) of the said method.

The invention further relates to a fiber-web, obtainable by the method of the invention, namely in step d).

In some embodiments of the invention, the fiber-web further comprises a coating or impregnation with soluble portion (plant extract) of herbs, medicinal plants, tea, vegetables dye plants and/or spices.

The coating or impregnation is obtained by various methods known to the skilled person, such as applying to or treating the fiber-web or sheet-like structure with a plant extract, such as in a bath or by special application means, such as sprayers. In addition, various other ingredients, such as flavor or color treatments, can also be applied to the web. If applied with the soluble portion and/or other ingredients, the fibrous sheet material can, in some embodiments, then be dried using, for example, a tunnel dryer, to provide a sheet having a typical moisture content of less than 20% by weight, and particularly from about 9% to about 14% by weight.

The invention thus also relates to an impregnated or coated fiber-web, obtainable by the method of the invention, namely in step g).

According to a further embodiment, the fiber-web of the invention further comprises a coating or an impregnation with the soluble portion (plant extract) of said herbs, medicinal plants, tea, vegetables dye plants and/or spices. In another embodiment of the invention, the fiber-web of the present invention is obtainable by the method disclosed herein, namely as the end product in step g) of said method.

The products of the invention enable a more efficient extraction (up to about 100% solubles can be extracted from the plant) in the sense that more solubles can be released than natural plant ingredients for a given weight of material. The products also provide a faster extraction (than with a conventional extraction made from the vegetal material in its natural non converted form). Specifically, the compositions of the invention have improved efficiency, e.g. in boiling water or in non-heated water or water at room temperature.

The process for making the compositions of the invention also allows for specifically adjusting the final composition of the products, such as to remove from the soluble or the non-soluble portion(s) for example foreign matters, components altering odor or caffeine, pesticides, heavy metals, mycotoxins, toxicants and allergenic molecules such as coumarin, farnesol, geraniol, limonene, linalol, safrole, methyleugenol, or by adding to the soluble or the non-soluble portion(s) for example desirable additives, such as antiseptics, flavors, insect repellents, soothing agents.

In another embodiment, the soluble portion in the reconstituted material of the invention can be precisely adjusted (decreased as compared to standard level, at standard level, or increased as compared to standard level). A key benefit is that the level of ingredients in the reconstituted material can be precisely increased to a level higher than in the original natural form, thus allowing for products with a higher concentration of desired substances. The adjustment of ingredients can also guarantee a consistent, standardized level of delivered ingredients to compensate natural variations of substances, i.e. active ingredients, in plants.

Preferably, the method of the invention also allows for reduction of undesired compounds from the material, such as to selectively remove undesired components (natural ingredients, pesticides, impurities or the like). For example, it is possible to remove components from either the soluble portion (plant extract) or from the non-soluble portion (solid plant particles) or both by liquid-liquid extraction, physical adsorption, centrifugation, chromatography, crystallization, decantation, by use of a demister, drying, distillation, electrophoresis, elutriation, evaporation, solid phase or liquid-liquid extraction, flotation, flocculation, filtration (for example using membranes), vapor-liquid separation, and/or sublimation and other means well known to the skilled person, preferably before applying the plant extract to the base web.

In connection with adding ingredients, extracts of different sources and origins, flavors, coloring agents or the like may be used, such as clorophyll, anthocyans, caramel, caroteinoids.

The present invention also allows to blend various plants and herbs, e.g., for specific medicinal, cosmetic, coloring or dermatologic purposes. In one example, instead of using single plants, such as tea or mint leaves, tea may be replaced by a mixture of, for example, 50% green tea (*Camellia sinesis*) and 50% mint (*Mentha piperita*) leaves (w/w) for refreshing applications; 50% mate (*Ilex paraguariensis*) and 30% ivy (*Hedera helix*) leaves and 20% *coffea* beans (*Coffea spp*) for slimming applications (w/w); 40% *Gingko biloba* leaves and 40% *Curcuma longa* rhizome and 20% rosemary (*Rosmarinus officinalis*) leaves for anti-aging purposes (w/w); 40% black tea (*Camellia sinensis*) and 30% *hibiscus* flower (*Hibiscus sabdariffa*) and 30% hazel (*Corylus avellana*) leaves for skin coloration (w/w); and many other combinations.

The combination of different plant materials through the reconstitution process into a single fiber web impregnated with extracts from different plants (the same plant or blends) offers additive or synergistic effects. For example, it is known that combinations of certain plant extracts or combinations of certain plant ingredients have additive or synergistic effects, such as, for example, a mixture of hops and valerian extracts for use in treating insomnia and vigilance (Blumenthal and al., J. Herbal Medicine, expanded Commission E monographs, American Botanical Council, Austin, 2000, 394-400), or mixtures of oregano and cranberry extracts for use in treating *H. pylori* infections (Lin et al., Appl. Environ. Microbiol. December 2005, vol. 71, no. 12, 8558-8564), or different mixtures of extracts of *S. baicalensis, D. morifolium, G. uralensis* and *R. rubescens* tested for their additive or synergistic effect in prostate cancer cell lines (Adams et al., Evid Based Complement Alternat Med. 2006 March; 3(1): 117-124).

The production method also provides for reducing microbiological load of the final products because of the high temperatures during the papermaking process.

The products of the invention provide a light material having a small surface, which allows economic packaging/shipping. For the consumer, the products of the invention are easy to transport and easy to use. Specifically, it has been found that the products of the invention are easily extractable even in cold water. This has particular advantages for consumers in cases where no heating or electricity is available for preparing hot water.

The products are further available in all shapes, dimensions and formats, such as leaves, sticks, discs and the like, and can be customized with a logo.

In sum, the reconstituted plant products of the invention provide several benefits and advantages, such as the provision of products with higher extraction yield and extraction speed;

the provision of a preferably dispersible and biodegradable product;

the ability to adjust the content of active ingredients (such as polyphenols, essential oils and the like) to provide a consistent composition;

the ability to adjust (reduce) the content of undesired constituents (such as pesticides, caffeine and the like);

the ability to provide new sensory characteristics (such as adjusting intensity of flavor, mixture of various plants and the like); and reduction of the bacterial load during the manufacturing process.

The following examples further describe and demonstrate embodiments that are within the scope of the present invention. The examples are given solely for the purpose of illustration, and are not to be construed as limitations of the present invention since many variations thereof are possible without departing from its spirit and scope.

EXAMPLES

Example 1

Method of Making the Reconstituted Plant Product

As raw material a black tea plant was used. The plant was mixed with water with a plant/water ratio of 1 to 5 by weight and the mixture was heated at 85° C. for 20 minutes. Subsequently, the aqueous portion was separated from the fibrous portion by an extraction step in a hydraulic press. Afterwards, the fibrous residue was again heated at 85° C. for 10 minutes with a plant/water ratio of 1 to 5 by weight. Again, the aqueous portion was separated from the fibrous portion by an extraction step in a hydraulic press. Then, the samples were refined in a Valley beater at 1.4% consistency for 10 minutes. As a next step, cellulosic fibers and in particular (a blend of abaca, hardwood and softwood pulps, with the respective ratios: 60/10/30) were added to the fibrous residue with a fibrous residue/woodpulp ratio of 5 to 1 in weight and hand sheets were made. The aqueous portion, which was separated by pressing, was concentrated in an evaporator to a solid concentration of 50%.

The concentrated aqueous portion was coated on the hand sheets on a manual size-press. The soluble level is typically between 27 and 37% in dry finished product. The soluble level of the reconstituted plant was approx. 27%, which is the soluble content of conventional plant used as the starting material of the experiment. The coated hand sheets were dried on a plate dryer. The obtained reconstituted plant product had the form of discs.

Comparison of Reconstituted Plant Product Versus Conventional Plant

It is well known that caffeine is a main component of tea leaves. Literature indicates that concentration may vary from 2.5 to 5% (w/w). Caffeine is a central nervous system and metabolic stimulant, and is used both recreationally and medically to reduce physical fatigue and to restore alertness when drowsiness occurs. It produces increased wakefulness, faster and clearer flow of thought, increased focus, and better general body coordination. It's often included in skin-care products with claims that it will reduce cellulite and puffy eyes.

Detection and quantification of caffeine can be performed through UV detection at 274 nm wavelength.

The obtained reconstructed plant was tested for its properties. Also, a conventional black tea plant was packed into a conventional cellulosic bag for preparing a comparison infusion. For determining the properties the optical density of the solutions were measured at 274 nm. Both the reconstructed plant and the conventional plant were inserted into hot water (90° C.). Same weights of plant material and identical experimental conditions were used. A beaker was filled with 200 ml water (ref. Cristaline) and was heated at 90° C. At the starting point of the experiment, i.e. T=0, the heating was stopped and the bag with conventional black tea was immersed into water. To homogenize the content of the beaker during the entire experiment, a rotary magnet was used.

In steps of 30 seconds six samples of the water were taken. Then, the optical density of the sample was determined using a spectrophotometer at the wavelength of 274 nm. For the reference test a sample of clear water (Cristaline) heated at 90° C. was used. Then the same procedure was repeated with the bag comprising the reconstituted plant product according to the invention.

Figure 3:
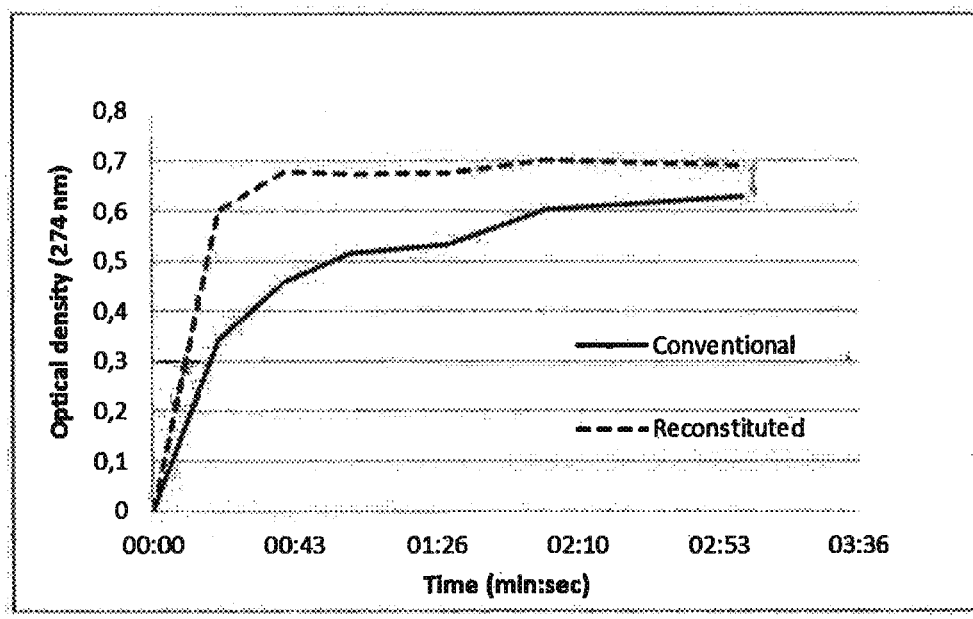
FIG. 3 is a graph showing total extraction time in hot water for an impregnated plant product as compared to a conventional plant in a bag.

As can be taken from FIG. 3, the optical density measured after 3 minutes of extraction for the reconstituted plant product was 0.69, whereas for the conventional plant 0.63 was measured. Hence, the product according to the invention provided a higher extraction rate of solubles, e.g. caffeine, as compared to a conventional plant product. In particular, the extraction ratio in this test was +10% as compared to the conventional bag. The reconstituted plant enabled a more efficient extraction (up to about 100% solubles were extracted from the plant). In other words, using the same amount of material, more solubles, e.g. caffeine, could be released from the reconstituted plant product according to the invention than from the conventional plant product in a standard cellulosic bag.

Similar results were obtained with different extraction times, or when the reconstituted plant was compared to natural black tea in loose form, i.e. without a cellulosic bag.

The above findings show the improved properties of the reconstructed plant. These findings, namely the improved substance release, are equally meaningful for other applications, e.g. with a different solvent or without a solvent.

Example 2

The reconstituted plant product obtained according to the method as explained in example 1 was used to determine a first extraction rate. On the other hand, natural black tea in a conventional cellulosic bag was used to determine a second extraction rate. The first and second extraction rates are representative of the speed soluble substances, mainly caffeine in this example, can be released from the plant products. The result is graphically shown in FIG. 4.

Figure 4:
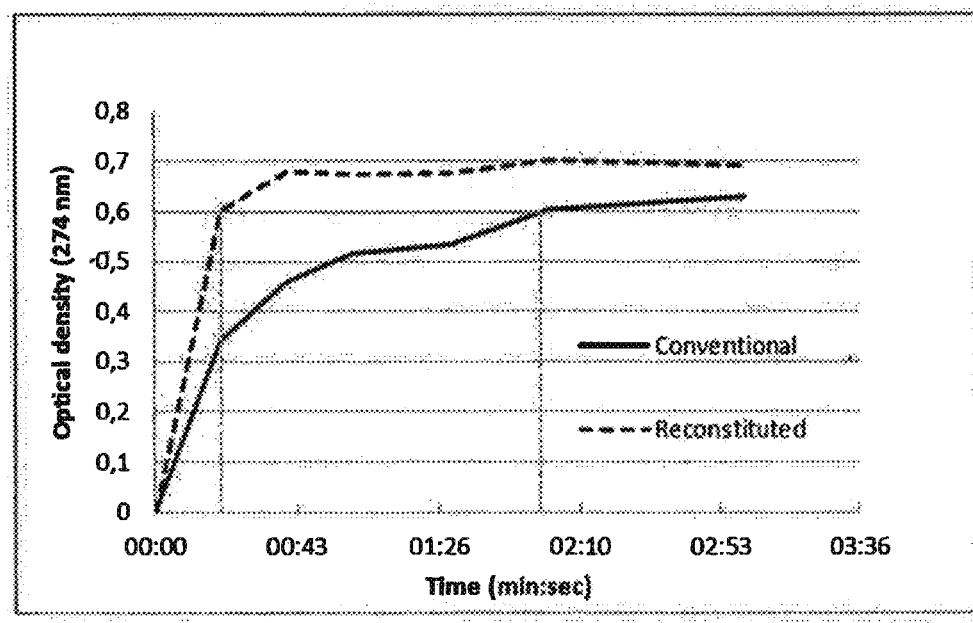
FIG. 4 is a graph showing total extraction time in hot water and the improved properties as regards the rate substances are released from the product according to the invention.

Like in example 1, the reconstituted plant was immersed into water at 90° C. and the optical density was measured over time. Likewise, the conventional plant product was immersed into water at 90° C. The more solubles, mainly caffeine in this example, are released from the plant, the higher the optical density of the respective water will be. As shown in FIG. 4, the optical density of the water with the reconstituted plant (dashed line) changes faster than the water with the conventional plant (continuous line). An optical density of 0.6 was reached by the reconstituted plant within 20 seconds. In contrast, the same optical density was reached by the conventional plant only after about 2 minutes.

This again shows that the reconstituted plant provides improved properties as regards the rate substances (mainly caffeine in this example) can be released from the plant product.

Similar results were obtained when reconstituted plant product was compared to natural black tea in loose form.

Example 3

In this example exactly the same setup was used as in example 2, only the water was at room temperature, i.e. 20° C.

Figure 5:
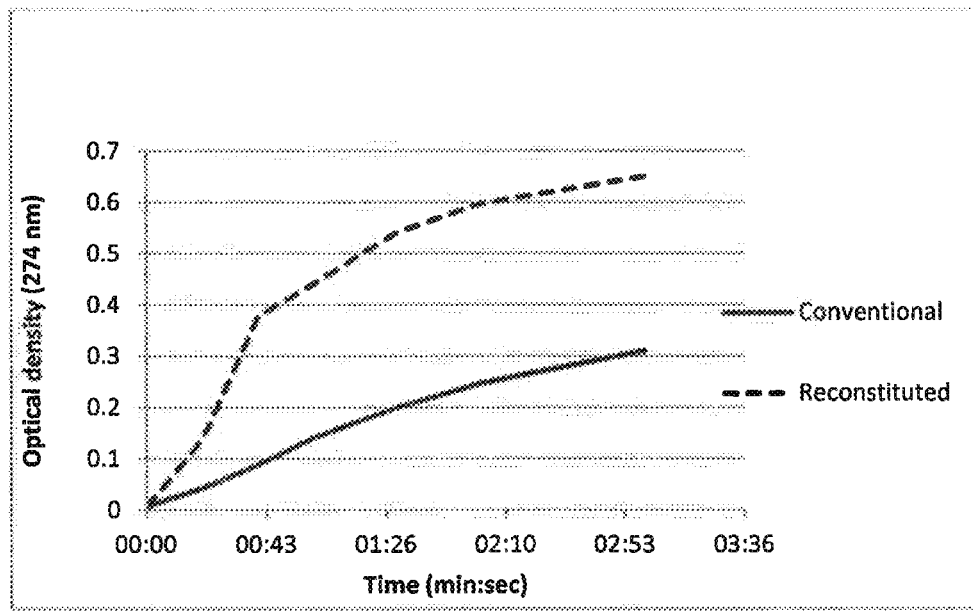
FIG. 5 is a graph showing total extraction time in cold water for an impregnated plant product as compared to a conventional plant in a bag.
Figure 6:
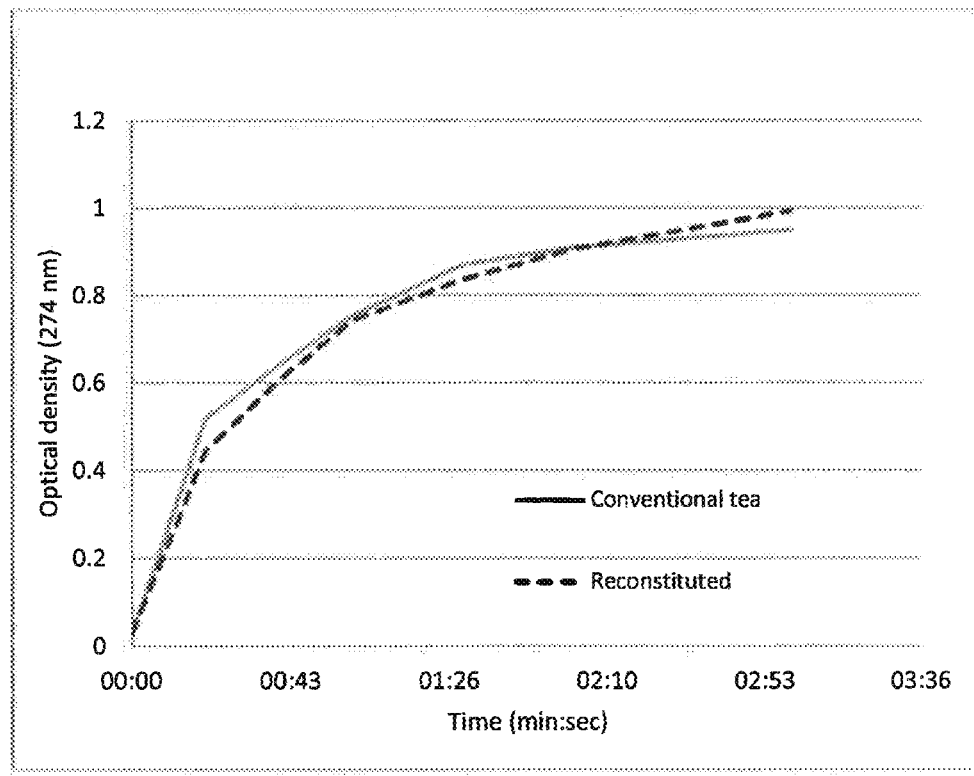
FIG. 6 is a graph showing extraction performance of a plant bag of the invention filled with conventional plant as compared to the extraction performance of a standard cellulosic plant bag filled with conventional plant.

As shown in FIG. 5, the optical density of the water with the reconstituted plant (dashed line) changes faster than the water with the conventional plant (continuous line). The water with the reconstituted plant reached an optical density of 0.3 within about 30 seconds and an optical density of 0.6 within about 2 minutes. In contrast, the conventional plant in a bag required about 6 times longer to provide the optical density of 0.3. Hence, the reconstituted plant product provides faster extraction of solubles, mainly caffeine, than conventional plant in bags.

Similar results were obtained when reconstituted plant was compared to natural black tea in loose form.

Example 4

This example shall demonstrate the adjustability (higher or lower than a standard) of the amount of solubles and active ingredients present on the reconstituted plant product. The soluble content was measured by determining the weight of a given sample before and after extraction.

Black tea was used to produce a reconstituted plant product according to the method of example 1. As control, a conventional black tea was used containing solubles in an amount of 26% (w/w).

By adjusting the coating ratio, the amount of solubles was adjusted in three different runs to 5% (w/w; decreased level), to 26% (w/w; standard level) and to 50% (w/w; increased level).

Due to the adjustability of the reconstituted product according to the invention it is possible to provide a consistent, standardized delivery level of soluble/active ingredients as compared to the natural products that generally show an inherent variability.

Example 5

In this example different reconstituted plant products were manufactured according to the method of example 1 and tested.
Sample 1 (Original plant in loose form)

For natural black tea in loose form the amount of solubles was determined to be around 30%.
Sample 2 (Original plant in cellulosic bag)

For natural black tea, i.e. the same as in Sample 1, in a conventional double chamber cellulosic bag the amount of solubles was determined to be around 30%.
Sample 3 (Reconstituted plant with standard amount of solubles)

A reconstituted plant product according to the invention was made from black tea. The reconstituted plant product was in the form of disks and had a standard dry basis weight, i.e. 100 gsm. The amount of solubles, which corresponds to the coating ratio for the reconstituted sample, was the same as of the natural plant, i.e. 30%.
Sample 4 (Reconstituted plant with decreased amount of solubles)

A reconstituted plant product according to the invention was made from black tea. The reconstituted plant product was in the form of disks and had a standard dry basis weight. The amount of solubles was 20% and thus decreased in comparison with the standard of 30%.
Sample 5 (Reconstituted plant with increased amount of solubles)

A reconstituted plant product according to the invention was made from black tea. The reconstituted plant product was in the form of disks and had a standard dry basis weight. The amount of solubles was 50% and thus increased in comparison with the standard of 30%.
Sample 6 (Reconstituted plant with decreased dry basis weight)

A reconstituted plant product according to the invention was made from black tea. The reconstituted plant product was in the form of disks and had a decreased dry basis weight of 60 gsm as compared to the standard dry basis weight of 100 gsm. The amount of solubles was the same as of the natural plant, i.e. 30%.

A comparison of the properties of the samples, in particular a comparison of sample 3 with samples 1 and 2; sample 3 with samples 4 and 5; and sample 3 with sample 6, confirmed the findings of the foregoing examples. That is, the reconstituted plant provides a better ratio of extraction and faster extraction and allows to adjust the amount of solubles/active ingredients (such as caffeine for tea) released.

Example 6

Method of Making a Bag Comprising Reconstituted Plant Product

Black tea was mixed with water with a plant/water ratio of 1 to 5 by weight and the mixture was heated at 85° C. for 20 minutes. Subsequently, the aqueous portion was separated from the fibrous portion by an extraction step in a hydraulic press. Afterwards, the fibrous residue was again heated at 85° C. for 10 minutes with a plant/water ratio of 1 to 5 by weight. Again, the aqueous portion was separated from the fibrous portion by an extraction step in a hydraulic press. Then, the samples were refined in a Valley beater at 1.4% consistency for 10 minutes. As a next step, cellulosic fibers (a blend of abaca, hardwood and softwood pulps, with the respective ratios: 60/10/30) were added to the plant fibrous residue at various levels in order to prepare the different samples and make hand sheets. Hand sheets were later dried on a plate dryer.

The following ratios of plant/cellulosic fibers have been used for producing a bag:
first sample: 40/60 (w/w);
second sample 60/40 (w/w);
third sample 80/20 (w/w).
No plant extract was located on the bags but the sample bags were filled with conventional black tea.

Comparison of Bag Comprising Reconstituted Plant Product Versus Conventional Cellulosic Bag A bag produced according to the above method was compared to a conventional cellulosic bag containing the same amount of black tea.

The outcome was similar to examples 1 and 2. As can be taken from FIG. 6, the extraction performance of the sample corresponding to the 80/20 ratio (first sample) matched with the extraction performance of conventional cellulosic bags as measured by optical density.

Example 7

Plant extract from the extracting step was used to impregnate the fiber web of example 6 to obtain impregnated bags with an amount of plant extract from 5% to 50% of the total weight. The bags were filled with black tea.

The measurements of the extraction performance of the produced bags as compared to conventional cellulosic bags containing the same amount of plant revealed a similar outcome as examples 1 and 2. That is, from the bags according to the invention more solubles were released, and extraction rates were higher due to the additional release of substances from the coating (plant extract), in addition to natural extraction coming from the black tea which was contained in the bag.

One sample bag according to the invention was impregnated with plant extract as described above. Using water at 90° C., the product released 35% (w/w) plant solubles into the water.

Example 8

The following products were produced:
1) A product in the form of a plant bag was produced with about 5% solubles (w/w) and a dry basis weight of approx. 120 g/m² (w/w);
2) A product in the form of a plant bag was produced with about 5% solubles (w/w) and a dry basis weight of approx. 60 g/m² (w/w).

Both products were not filled with plant.

Figure 7:
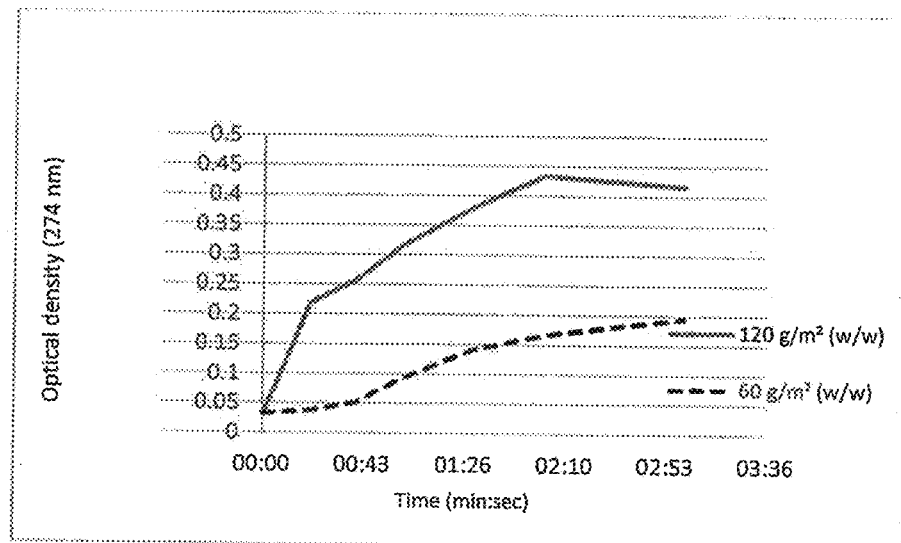
FIG. 7 is a graph showing extraction performance of a plant bag of the invention at a basis weight of 120 g/m$^2$ as compared to the extraction performance of a plant bag of the invention at a basis weight of 60 g/m$^2$.

As can be taken from FIG. 7, the first product comprising a dry basis weight of approx. 120 g/m² (w/w) releases more substances in shorter time as the second product comprising a lower dry basis weight of approx. 60 g/m² (w/w).

Example 9

Example 1 described above was repeated with the additional use of a wet strength agent (here: cationic polyamide amine resin), in order to reduce potential degradation of some of the reconstituted material in water. The wet strength agent was added to the fibrous portion.

A tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, soluble level of the reconstituted tea was approx. 27%, which is the soluble content of conventional tea used as the starting material of the experiment. The coated hand sheets were dried on a plate dryer. Infusion trials were run in hot water (approx. 90° C.) and product with wet strength agent showed less degradability into water than same material without agent.

Figure 8:
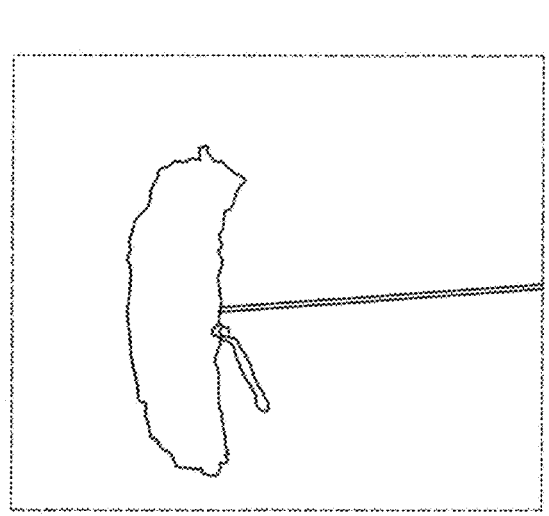
FIG. 8 shows reconstituted tea in one example without the use of a wet strength agent after 3 mins of infusion. The photograph shows that material is degraded.

FIG. 8 shows reconstituted tea in one example without the use of a wet strength agent after 3 mins of infusion. The photograph shows that material is degraded.

Figure 9:
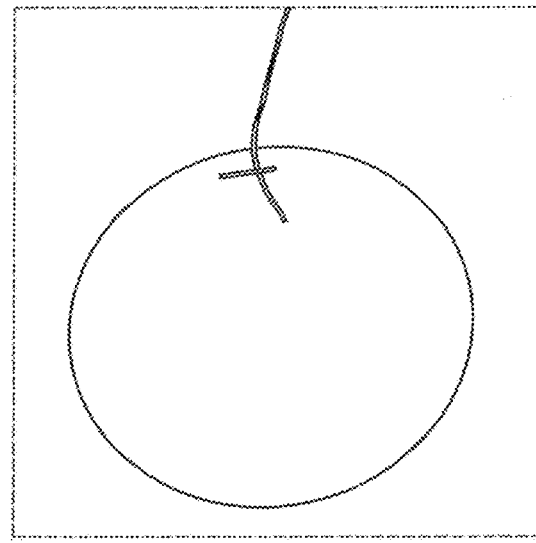
FIG. 9 shows reconstituted tea in this example with the use of a wet strength agent after 3 mins of infusion. The photograph shows that the material is substantially undegraded.

FIG. 9 shows reconstituted tea in this example with the use of a wet strength agent after 3 mins of infusion. The photograph shows that the material is substantially undegraded.

Example 10

In order to determine the effect of reconstituted tea soluble content and the dry basis weights on the infusion profile, a tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. The soluble level is typically between 27 and 37% in dry finished product. In this example, the following products were prepared:

Product A: soluble level of the reconstituted tea was 22%, which is the soluble content of conventional tea used as the starting material of the experiment. Dry basis weight of the material was 70 grs per m² (dry basis);

Product C: soluble level of the reconstituted tea was 22%, which is the soluble content of conventional tea used as the starting material of the experiment. Dry basis weight of this material was 170 grs per m² (dry basis) which is 143% higher than A;

Product D: soluble level of the reconstituted tea was 38% which is 73% higher than A. Dry basis weight of D material was 170 grs per m² (dry basis) also The coated hand sheets were dried on a plate dryer.

The products (A, C and D) obtained in this example were tested for their properties in preparing tea and compared. Both products were used to make tea, and the optical density of the solution (tea) was measured at 274 nm. For all samples, the total infusion time in hot water (90° C.) was 5 minutes. Same weights of tea material (2.5 grs) and identical experimental conditions were used: a beaker containing 500 ml water was heated at 90° C. At T=0, ie. upon start of the experiment, heating was stopped and a tea strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference/blank test was run with a sample of clear water heated at 90° C.

Figure 10:
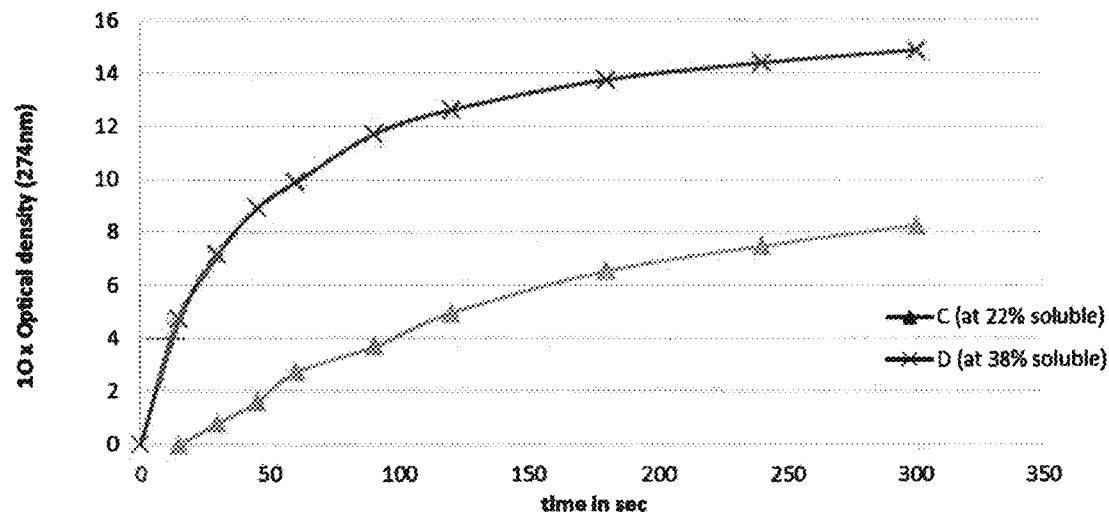
FIG. 10 shows a reconstituted material produced according to Example 10. Reconstituted tea (D—high soluble content) shows a higher infusion level of tea solubles than C (standard soluble level).
Figure 11:
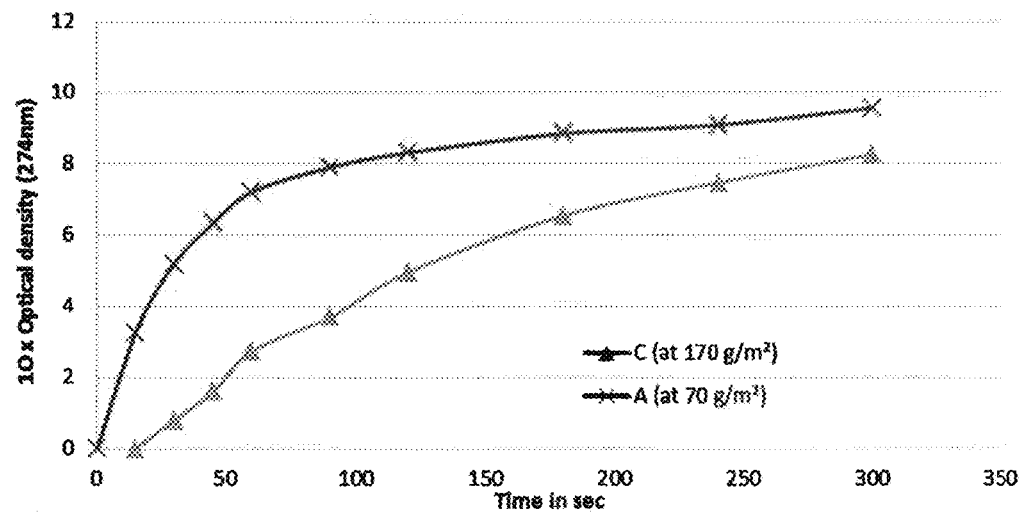
FIG. 11 shows a reconstituted material produced according to Example 10. Reconstituted tea A with a lower basis weight shows a faster infusion level of tea solubles than C.

The result is graphically shown in FIGS. 10 and 11.

FIG. 10: Reconstituted tea (D—high soluble content) shows a higher infusion level of tea solubles than C (standard soluble level). In order to reach an infusion level of 8.3 (expressed by 10× optical density at 274 nm), it takes 300 sec with sample C whereas only 40 sec are needed for D material (87% faster). Sensory evaluation performed by tea panel group also showed a stronger tea flavor and taste with D than with C after 5 mins infusion. This demonstrates that tea caffeine level can be adjusted in accordance with the soluble content of reconstituted tea material.

FIG. 11 shows that Reconstituted tea A with a lower basis weight shows a faster infusion level of tea solubles than C. Figures show that infusion rate of 8.3 (expressed by 10× optical density at 274 nm) is reached in 120 sec for A sample whereas 300 sec are needed for C. Infusion with A is 60% faster than with C. Actually, a lower basis weight for a given weight of material entails a more important contact surface which, at the end, improves caffeine infusion kinetics.

Example 11

In order to determine the effect of the reconstitution process on the green tea infusion sensory profile, a tea product was made according to the following method: a green tea (Sencha from China) was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the tea fibrous residue with a tea fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 36% extract content, which is the soluble content of the starting material of the experiment. The coated hand sheets were dried on a plate dryer.

Figure 12:
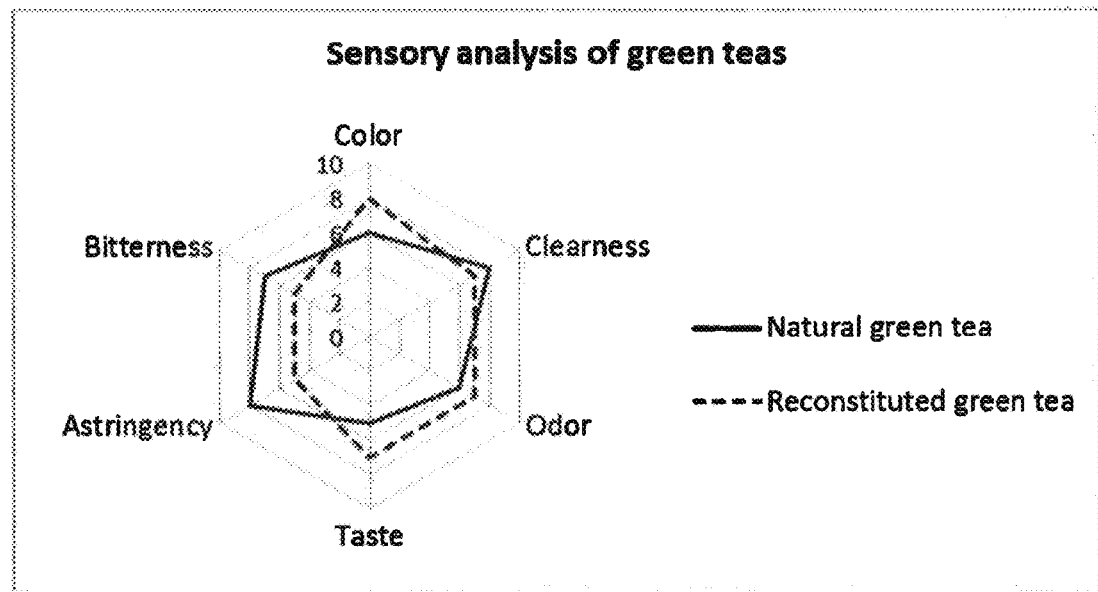
FIG. 12 shows the sensorial profile of reconstituted green tea and natural material.

The product obtained in this example was tested for its sensory properties and compared to natural tea material used for the experiment as described above. Both products were used to make tea. For all samples, the total infusion time in hot water (90° C.) was 5 minutes. Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 12.

The experiment shows that the odor, color and taste are higher in the reconstituted tea than in the natural material. However, astringency and bitterness are significantly lower in the reconstituted tea than natural material.

Example 12

Reconstitution of Rooibos Leaves

A reconstituted product was made according to the following method: Rooibos (*Aspalathus linearis*) was initially heated at 85° C. for 20 minutes with a rooibos/water ratio of 1 to 5 by weight. This was followed by an extraction step in a hydraulic press to separate the aqueous portion from the rooibos fiber portion. The recovered rooibos fiber portion was again heated at 85° C. for 10 minutes with a rooibos/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the rooibos fibrous residue with a rooibos fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 22% extract content, which is the soluble content of the starting material of the experiment. The coated hand sheets were dried on a plate dryer.

Figure 13:
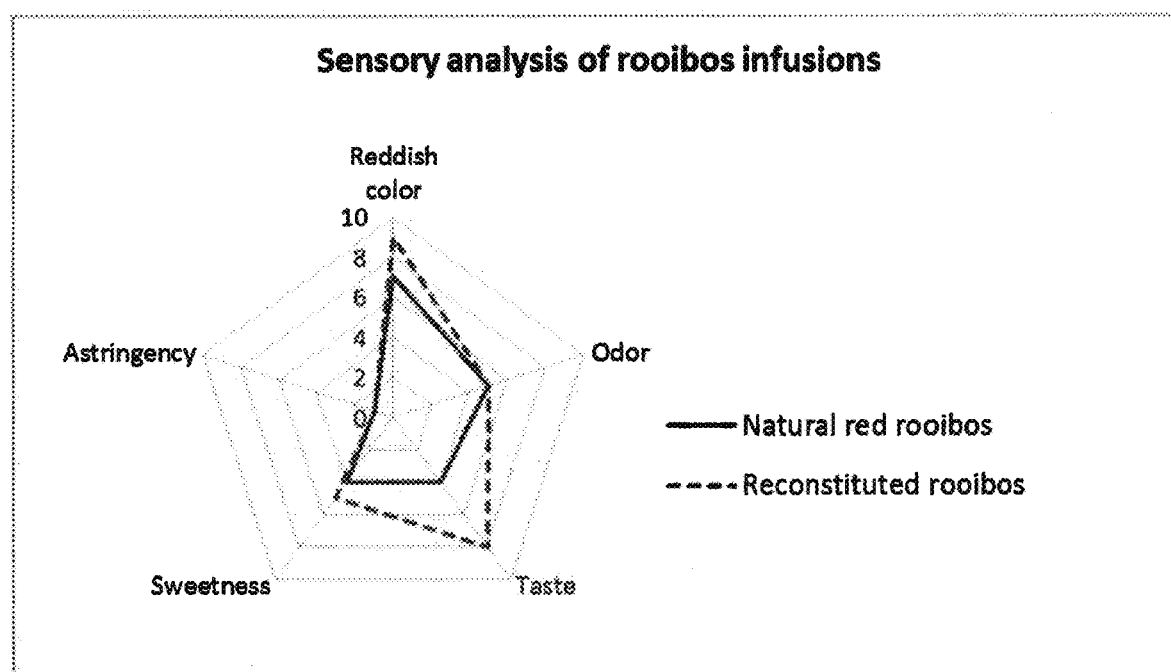
FIG. 13 shows the sensory analysis of reconstituted rooibos and natural material (rooibos leaves).

The product obtained in this example was tested for its sensory properties and compared to natural rooibos material used for the experiment as described above. Both products were used to make a rooibos beverage. For all samples, the total infusion time in hot water (90° C.) was 5 minutes. Same weights of rooibos material (2 grs) and identical experimental conditions were used: a beaker containing 200 ml water was heated at 90° C. and rooibos materials were immersed into water. Then, after 5 minutes, sensory profile of both products was performed. The result is graphically shown in FIG. 13.

The experiment demonstrates that reconstituted rooibos tea shows a stronger taste than original material. Moreover, color is stronger.

The reconstituted rooibos obtained in this example and its original material were tested for their properties in preparing infusion and compared. Both products were used to make infusion, and the optical density of the solution was measured at 450 nm. For all samples, the total infusion time in hot water (90° C.) was 5 minutes. Same weights of materials (2.5 grs) and identical experimental conditions were used: a beaker containing 500 ml water was heated at 90° C. At T=0, ie. upon start of the experiment, heating was stopped and a reconstituted rooibos strip was immersed into water. A rotary magnet was used to homogenize the content of the beaker during the entire experiment.

Rooibos is becoming more popular, particularly among health-conscious consumers, due to its its lack of caffeine and high level of antioxidants such as aspalathin, nothofagin and lutein. Lutein is a carotenoid, a reddish pigment contributing to the red color of rooibos. It also functions as an antioxidant and radical scavenger, specially for eyes. Rooibos is also used in skin products, and shows some evidence of sun-protective effects.

Detection and quantification of lutein can be performed through UV detection at 450 nm wavelength.

Samples of water were taken regularly and up to 5 minutes. Then, the optical density of the sample was determined using a spectrophotometer at the wavelength of 450 nm (maximum absorption of lutein). The reference/blank test was run with a sample of clear water heated at 90° C.

Figure 14:
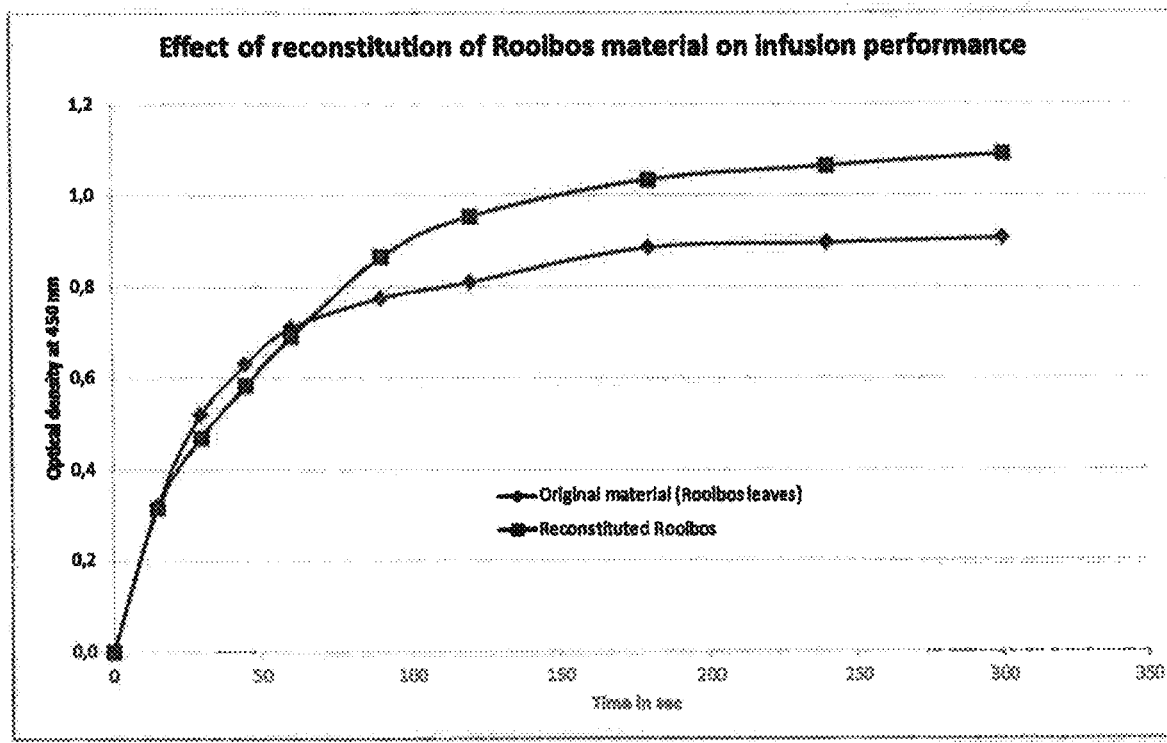
FIG. 14 shows the infusion performance of a reconstituted Rooibos material.

The infusion performance for reconstituted Rooibos material is graphically shown in FIG. 14. Infusions of rooibos products are comparable. However, it is demonstrated that reconstituted rooibos offers a more complete extraction, e.g., of lutein. After 5 mins infusion, optical density of liquor made of reconstituted rooibos is 1.1 compared 0.9 for original material (+22%).

Example 13

Reconstitution of Thyme Leaves

A reconstituted product was made according to the following method: Thyme (*Thymus vulgaris*) was initially heated at 85° C. for 20 minutes with a thyme/water ratio of 1 to 5 by weight. This was followed by an extraction step in a hydraulic press to separate the aqueous portion from the thyme fiber portion. The recovered thyme fiber portion was again heated at 85° C. for 10 minutes with a thyme/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the thyme fibrous residue with a thyme fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment.

Figure 15:
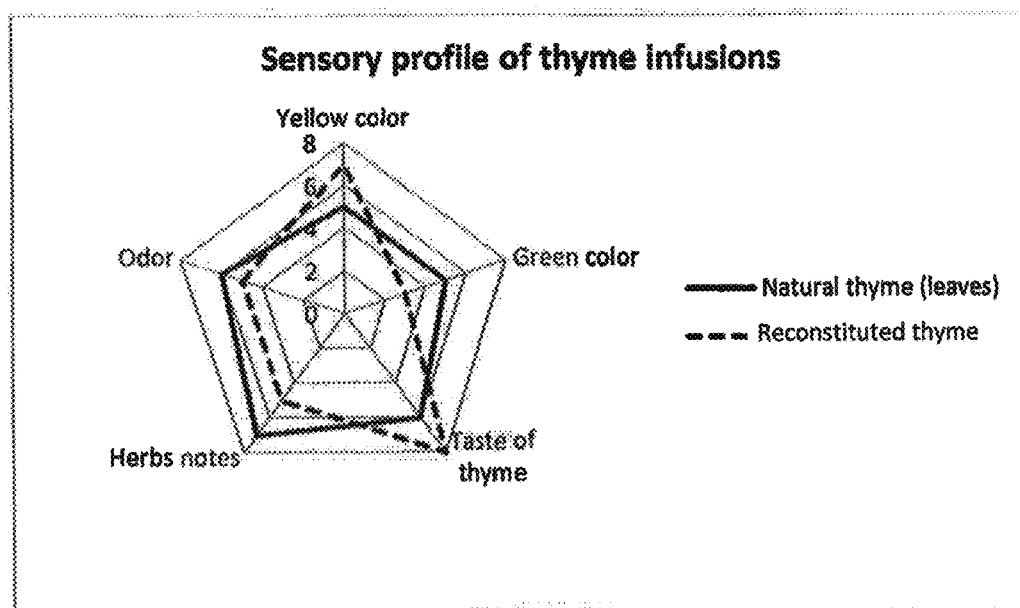
FIG. 15 shows the sensory profile of thyme leaves as compared to reconstituted thyme.

The coated hand sheets were dried on a plate dryer. The product obtained in this example was tested for its sensory properties and compared to natural thyme material used for the experiment as described above. Both products were used to make a thyme beverage. For all samples, the total infusion time in hot water (90° C.) was 5 minutes. Same weights of thyme material (2 grs) and identical experimental conditions were used: a beaker containing 200 ml water was heated at 90° C. and thyme materials were immersed into water. Then, after 5 minutes, sensory profile of both products was performed. The result is graphically shown in FIG. 15.

The experiment shows that that the color is rather yellow for the reconstituted thyme and rather green for the natural leaves. Global odor and herbal notes are higher for the natural thyme. However, the taste of thyme is higher in the reconstituted material.

The reconstituted thyme obtained in this example and its original material were tested for their properties in preparing infusion and compared. Both products were used to make infusion, and the optical density of the solution was measured at 326 nm. For all samples, the total infusion time in hot water (90° C.) was 5 minutes. Same weights of materials (2.5 grs) and identical experimental conditions were used: a beaker containing 500 ml water was heated at 90° C. At T=0, ie. upon start of the experiment, heating was stopped and a reconstituted thyme strip was immersed into water. A rotary magnet was used to homogenize the content of the beaker during the entire experiment.

Rosmarinic acid is a caffeic acid ester found in a variety of plants and especially in Thyme (*Thymus vulgaris*). It has antioxidant, medicinal and dermatological properties.

Detection and quantification of rosmarinic acid can be performed through UV detection at 326 nm wavelength.

Samples of water were taken regularly and up to 5 minutes. Then, the optical density of the sample was determined using a spectrophotometer at the wavelength of 326 nm (maximum absorption of rosmarinic acid). The reference/blank test was run with a sample of clear water heated at 90° C. The result is shown in FIG. 16.

Figure 16:
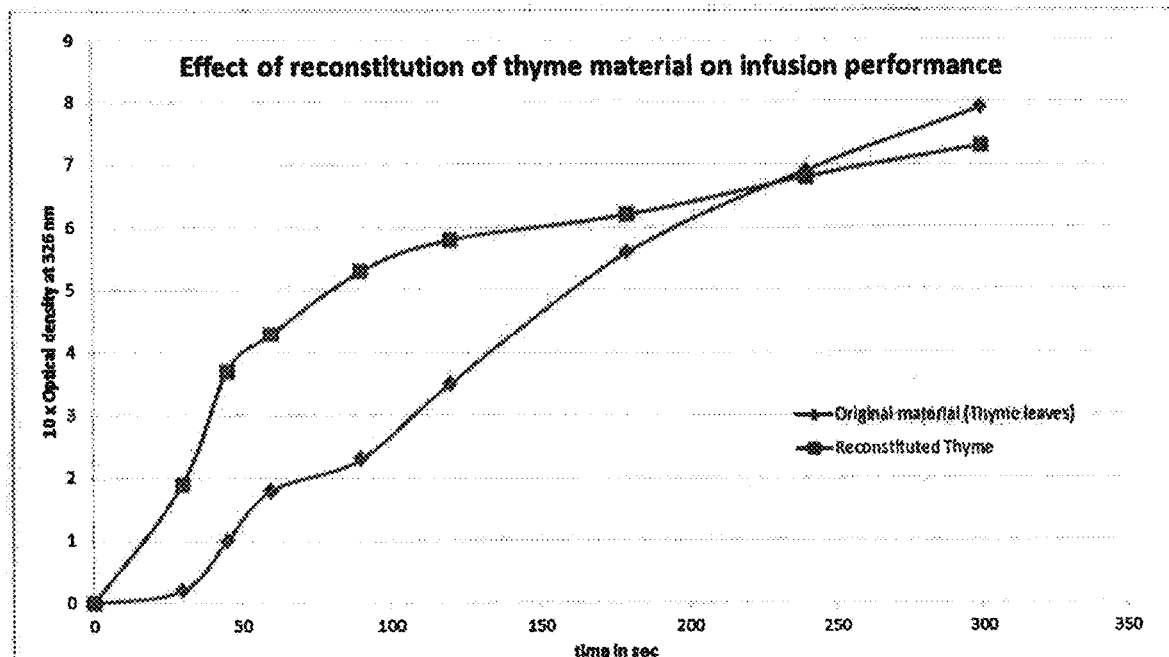
FIG. 16 shows the infusion performance of a reconstituted thyme material.

FIG. 16 shows that reconstituted thyme infusion occurs very quickly. After 90 sec infusion, optical density of original material is 2.3 whereas liquor from reconstituted thyme optical density is 5.3 which is 130% higher.

Example 14

Reconstitution of Thyme and Black Tea Leaves

A reconstituted product was made according to the following method: Thyme (*Thymus Vulgaris*) and black tea (*Camelia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/wood pulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 25% extract content, which is the balanced soluble content of the materials of the experiment. The coated hand sheets were dried on a plate dryer.

Figure 17:
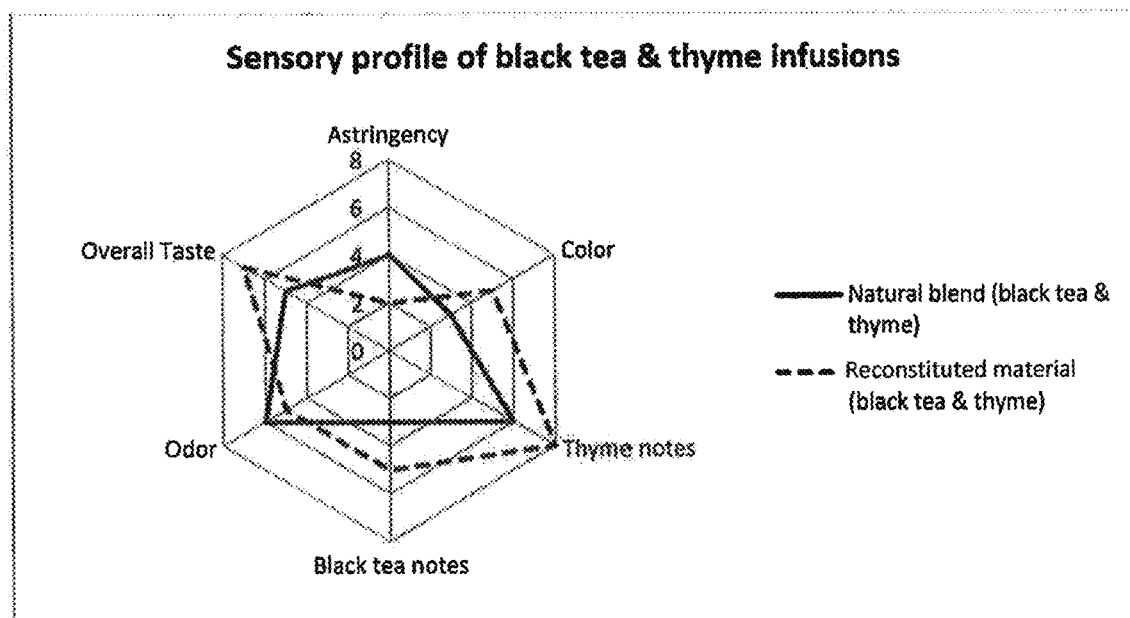
FIG. 17 shows the sensory analysis of reconstituted thyme & black tea as compared to the natural blend.

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 17.

The experiment shows that color and overall taste are higher in the reconstituted leaves. Also, thyme and black tea notes are higher. But the astringency of the product is lower in the reconstituted material.

Example 15

Reconstitution of Thyme and Laurel Leaves ("*Bouquet garni*")

A reconstituted product was made according to the following method: Thyme (*Thymus vulgaris*) and Laurel (*Laurus nobilis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 34% extract content which is the balanced soluble content of the materials of the experiment. The coated hand sheets were dried on a plate dryer.

Figure 18:
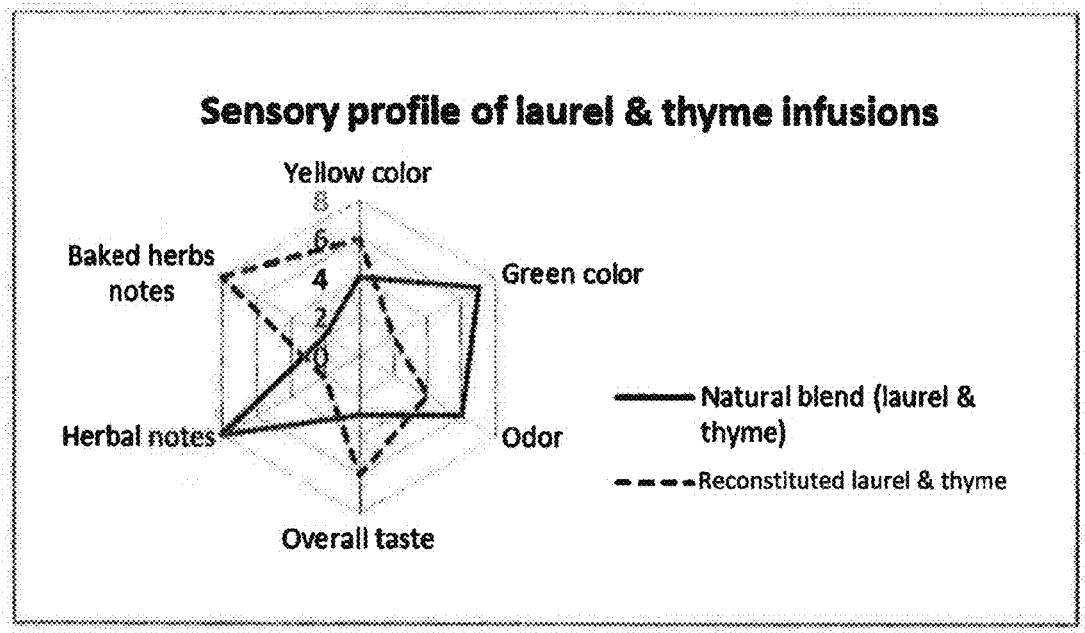
FIG. 18 shows the sensory analysis of reconstituted laurel & thyme vs natural blend (laurel & thyme leaves).

The product obtained in this example was tested for its sensory properties and compared to natural tea material used for the experiment as described above. Both products were used to make tea. For all samples, the total infusion time in hot water (90° C.) was 5 minutes. Same weights of tea material (2 grs) and identical experimental conditions were used: a beaker containing 200 ml water was heated at 90° C. and tea materials were immersed into water. Then, after 5 minutes, sensory profile of both products was performed. The result is graphically shown in FIG. 18.

The experiment shows that the two products are very different. The color is rather yellow for reconstituted product and green for the original blend. The taste is on the herbal side for the original blend and more on the baked side for the reconstituted material. Globally, taste and odor are higher for the original blend. Taste and odor can, however be adjusted and increased for the reconstituted material by increasing soluble content of reconstituted material or by adding ingredients such as food flavors, food dyes or other plant extracts having color and aroma properties.

Example 16

Reconstitution of Mint Leaves

A reconstituted product was made according to the following method: Mint (Mentha×piperita) was initially heated at 85° C. for 20 minutes with a mint/water ratio of 1 to 5 by weight. This was followed by an extraction step in a hydraulic press to separate the aqueous portion from the rooibos fiber portion. The recovered mint fiber portion was again heated at 85° C. for 10 minutes with a mint/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the mint fibrous residue with a mint fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 50% extract content, which is the soluble content of the starting material of the experiment. The coated hand sheets were dried on a plate dryer.

Figure 19:
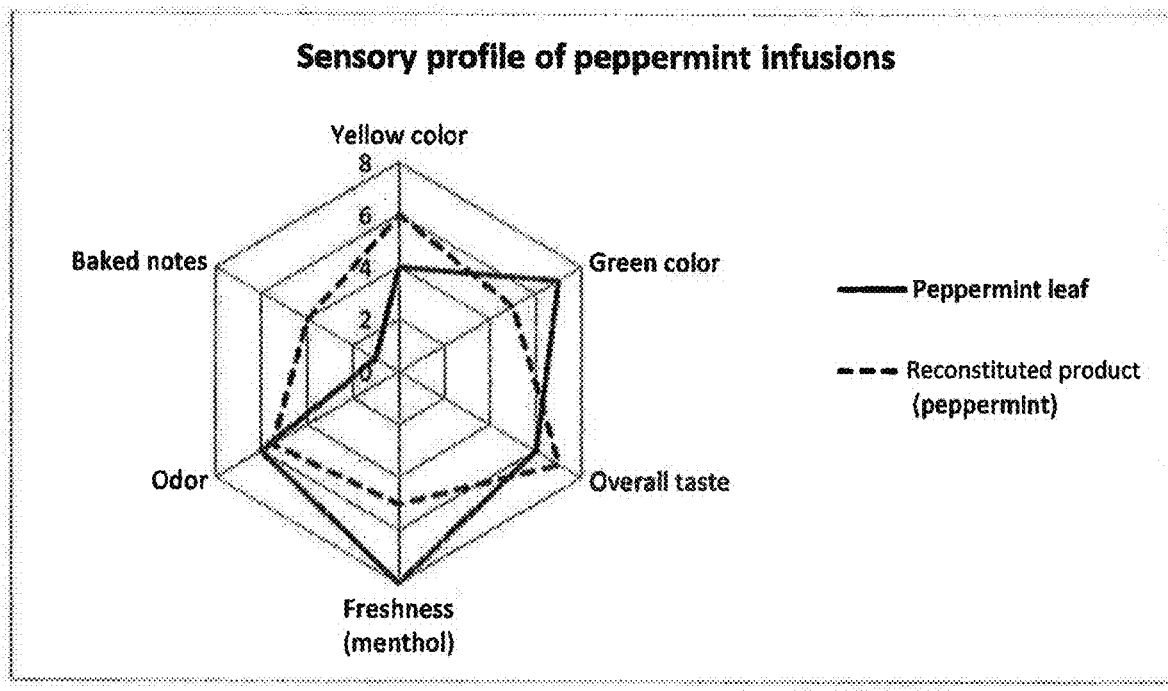
FIG. 19 shows the sensory analysis of reconstituted mint vs original mint material (*Menthaxpiperita*).

The product obtained in this example was tested for its sensory properties and compared to natural mint material used for the experiment as described above. Both products were used to make a mint beverage. For all samples, the total infusion time in hot water (90° C.) was 5 minutes. Same weights of mint material (2 grs) and identical experimental conditions were used: a beaker containing 200 ml water was heated at 90° C. and mint material was immersed into water. Then, after 5 minutes, sensory profile of both products was performed. The result is graphically shown in FIG. 19.

The experiment shows that in the reconstituted product, freshness/menthol notes have been reduced vs original mint material; however, overall taste is stronger.

Example 17

Reconstitution of Mint (Mentha×Piperita) and Green Tea Leaves (Camellia sinensis)

A reconstituted product was made according to the following method: Mint (Mentha×piperita) and Green Tea leaves (Camellia sinensis) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The recovered blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the blend fibrous residue with a blend fiber/wood pulp ratio of 5 to 1 in weight in order to make hand sheets. The aqueous portion was concentrated in an evaporator to a solid concentration of 50% and L-menthol was added to the solution at 6% and then coated on a hand sheet on a manual size-press. In this example, the product was produced at 35% extract content, which is the balanced soluble content of the materials of the experiment. The coated hand sheets were dried on a plate dryer.

Figure 20:
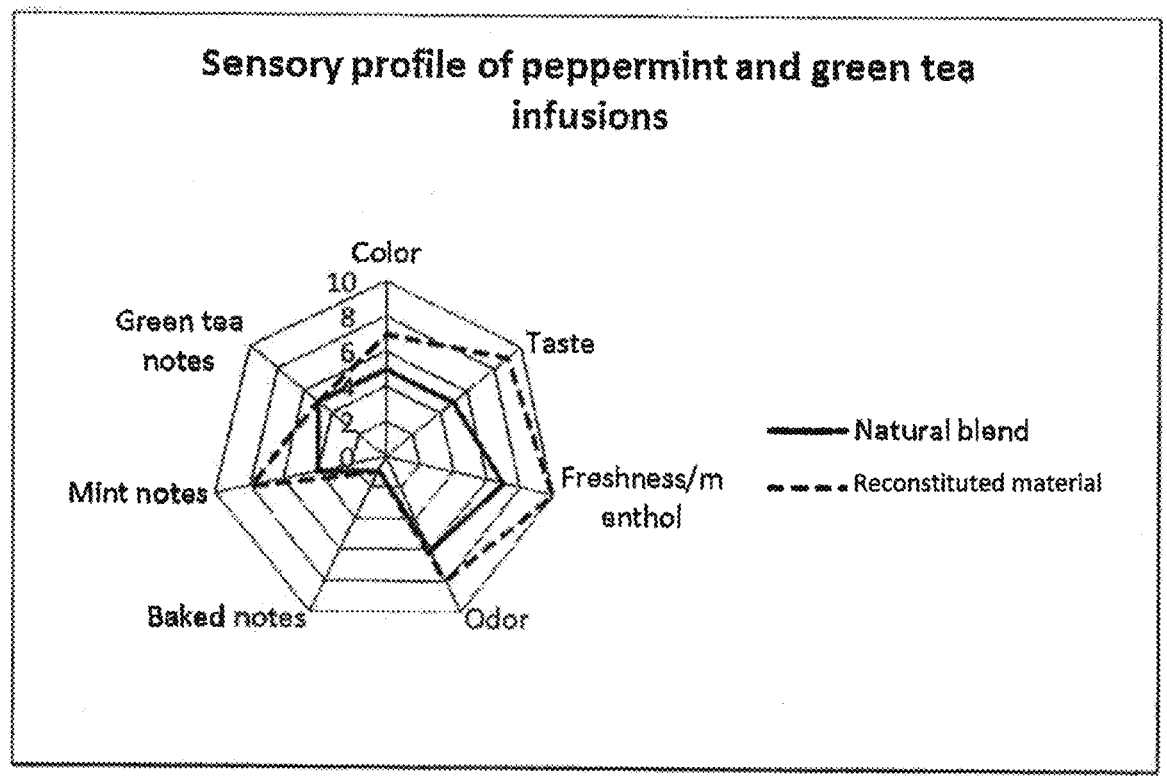
FIG. 20 shows the sensory analysis of reconstituted mint and green tea vs original blend.
Figure 21A:
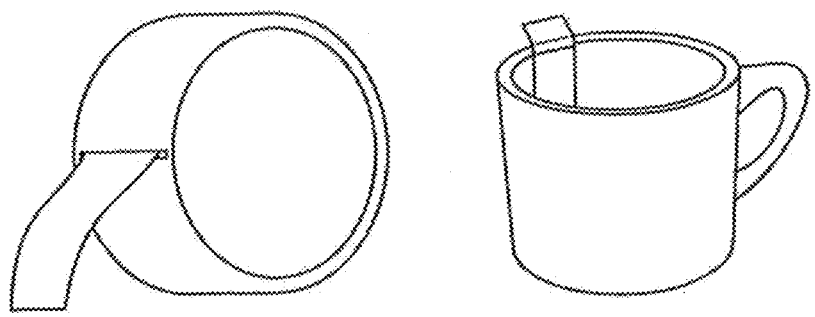
FIG. 21A-K shows reconstituted material in different physical shapes that provide for different kinds of applications.
Figure 21B:
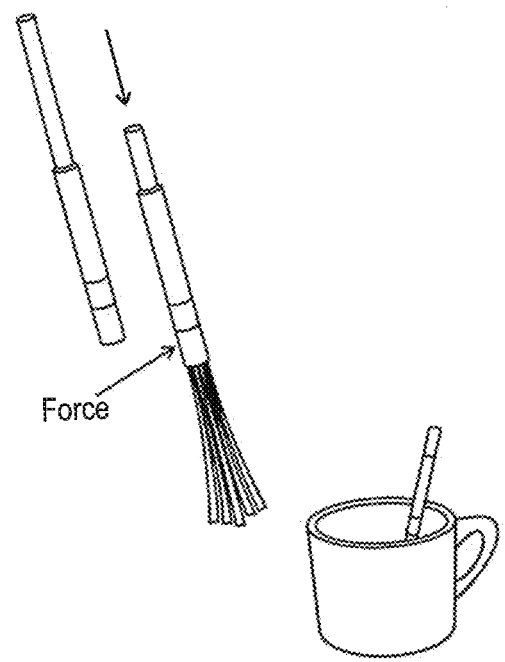
Figure 21C:
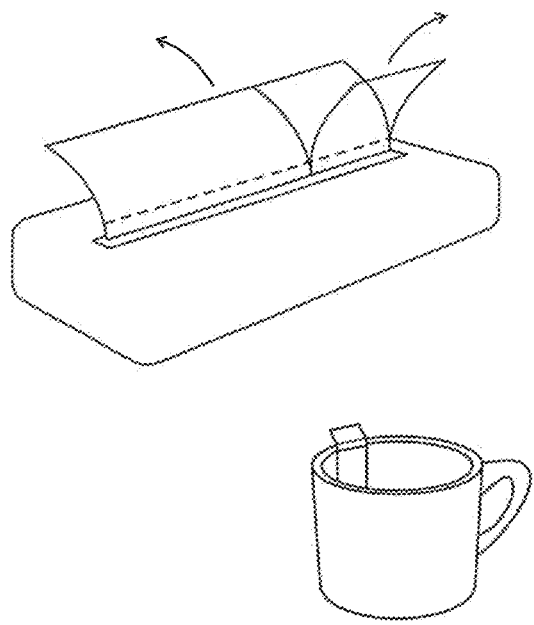
Figure 21D:
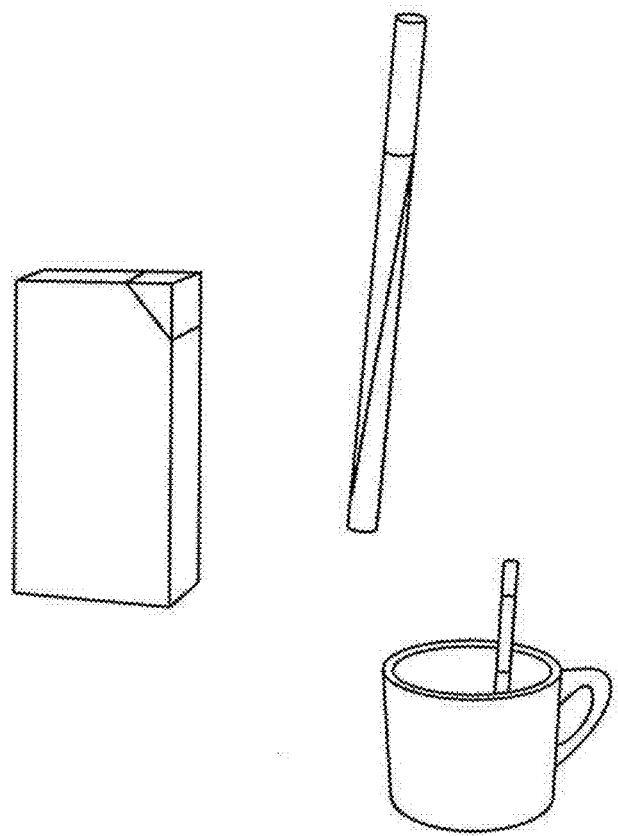
Figure 21E:
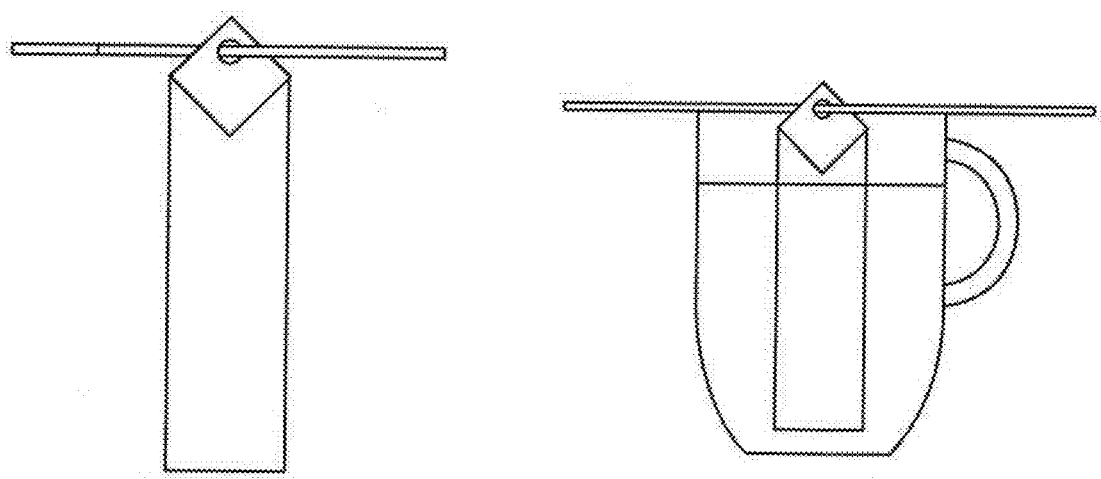
Figure 21F:
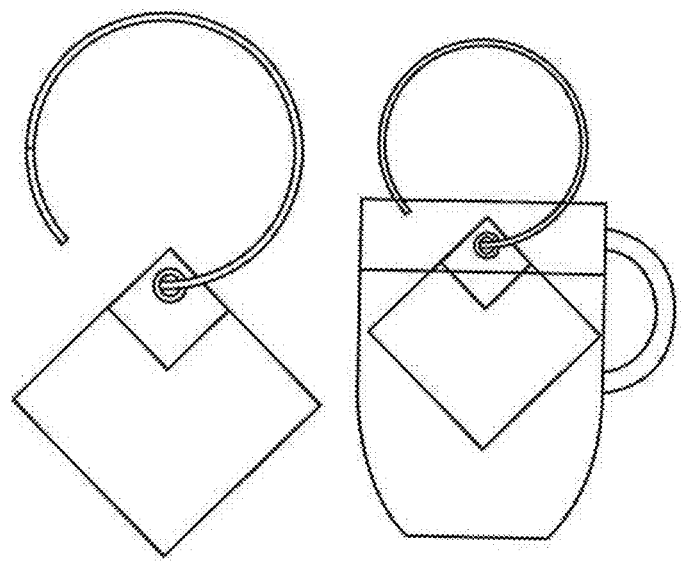
Figure 21G:
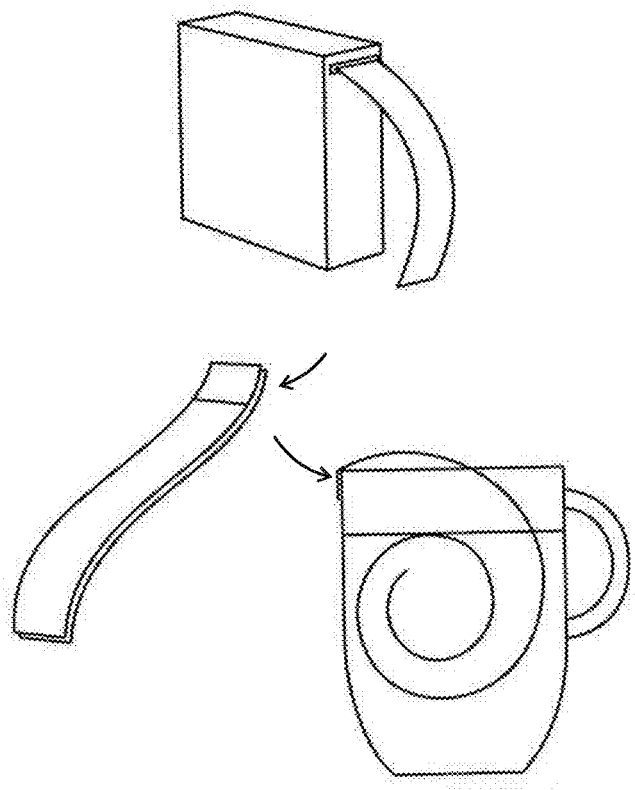
Figure 21H:
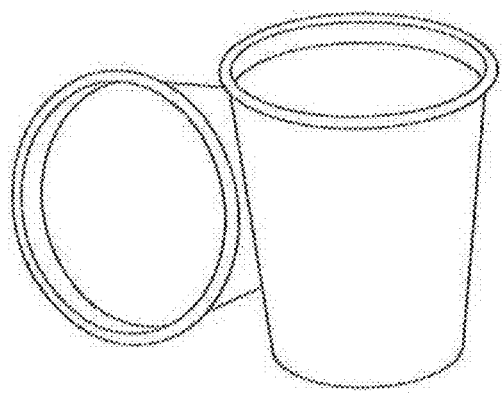
Figure 21I:
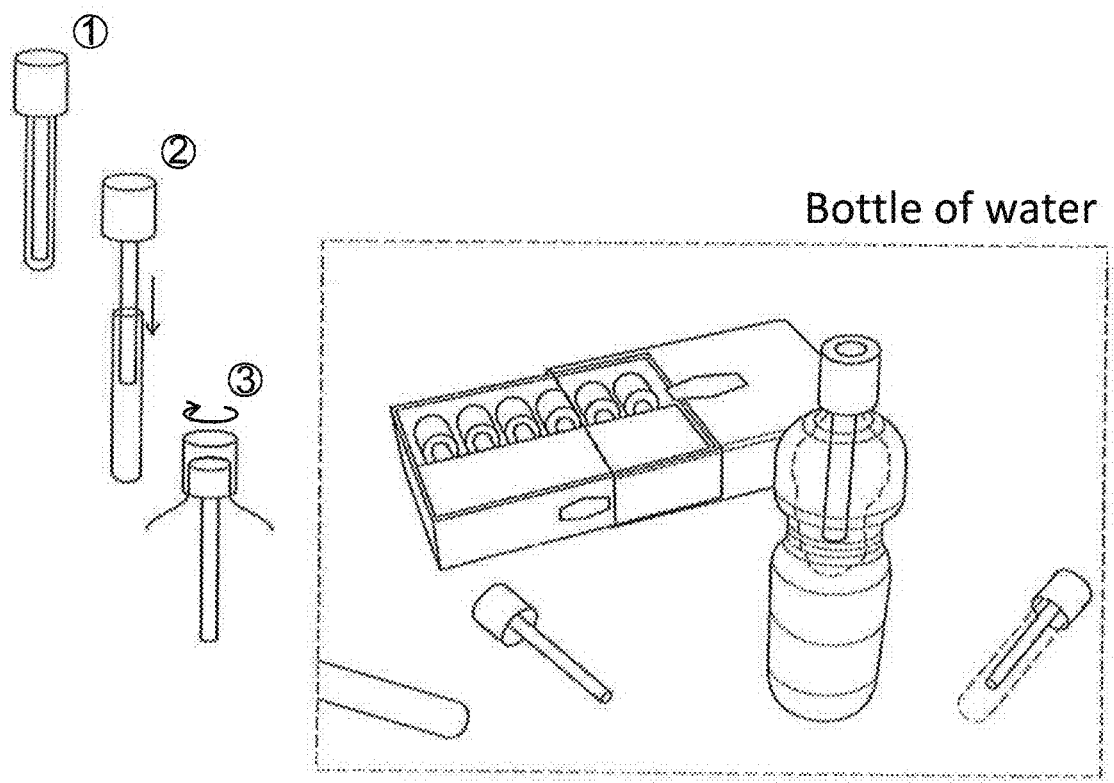
Figure 21J:
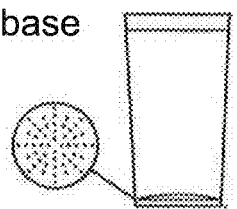
Figure 21J:
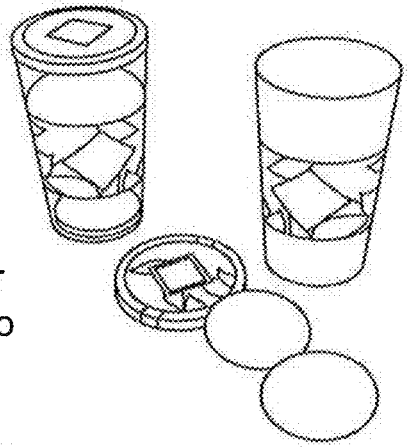
Figure 21K:
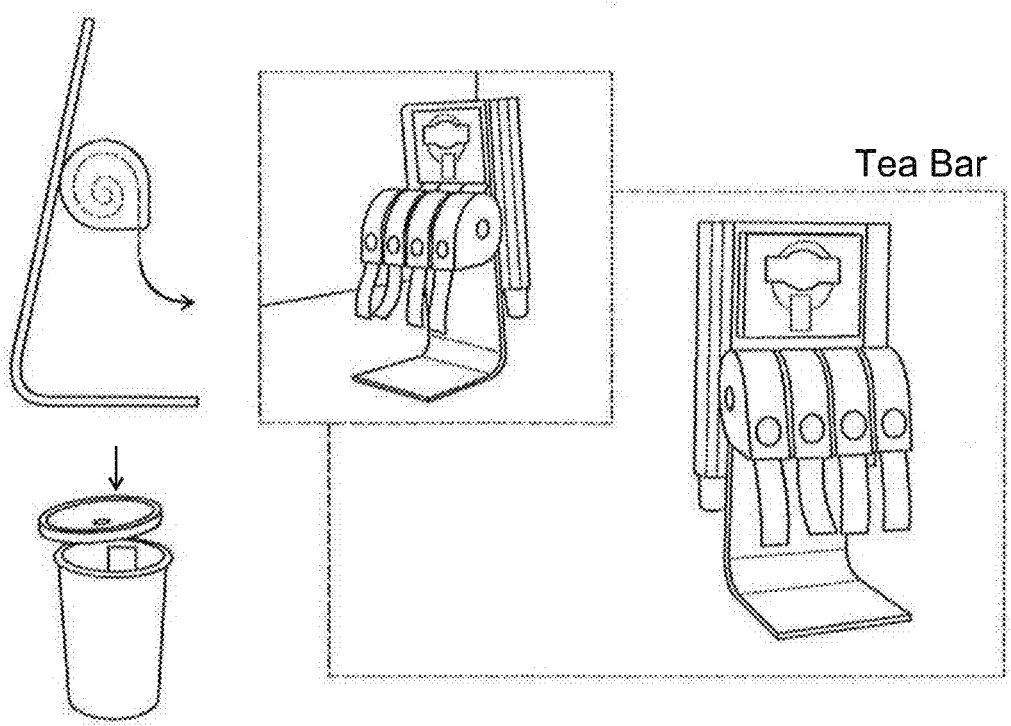

The product obtained in this example was tested for its sensory properties and compared to natural blend material used for the experiment as described above. Both products were used to make the infusion. For all samples, the total infusion time in hot water (90° C.) was 5 minutes. Same weights of material (2 grs) and identical experimental conditions were used: a beaker containing 200 ml water was heated at 90° C. and blend was immersed into water. Then, after 5 minutes, sensory profile of both products was performed. The result is graphically shown in FIG. 20.

Example 18

Removal of Caffeine from Tea Leaves Thanks to the Reconstitution Process

In order to illustrate the potential of the invention to reduce the amount of specific components from tea, a treatment to decrease caffeine content from tea was developed and tested at the lab scale.

Literature shows that alkaloids compounds such as caffeine are extracted in the soluble portion.

Therefore, experiment has been run on the liquor part of tea, after separation step.

A black tea was initially heated at 85° C. for 20 minutes with a tea/water ratio of 1 to 5 by weight. This was followed by an extraction step in a hydraulic press to separate the aqueous portion from the tea fiber portion. The aqueous portion of tea was then mixed with activated charcoal in powder form. Approx. 23 g of activated charcoal was added to 500 ml of tea liquor and mixed at 60° C., stirred at 350 rpm for 1 hour. After filtration, caffeine levels in liquors were measured then through LC-MS method.

The following samples were produced:
Control: standard tea liquor without activated charcoal treatment
A: Tea liquor treated with activated charcoal Acticarbone P13 from CECA
B: Tea liquor treated with activated charcoal Acticarbone 2SW from CECA
C: Tea liquor treated with activated charcoal Acticarbone 3SA from CECA
D: Tea liquor treated with activated charcoal Acticarbone CPL from CECA
Caffeine contents in tea liquors are as follows:
Control: 22700 mg/Kg
A: <10 mg/Kg
B: <10 mg/Kg
C: <10 mg/Kg
D: <14 mg/Kg
It can be seen that caffeine levels are strongly reduced by using activated charcoal on tea liquor.

Example 19

Reduction of Microbiological Load of Tea Through the Reconstituted Process

Reconstituted tea material produced during experiment 7 was analyzed vs original tea material. Bacteria counts were run (Aerobic Plate Count after 48 hrs at 30° C.). Results are shown in the following table:

| | Total Aerobic bacteria count (units/grs) |
|---|---|
| Original tea material | $8.3 \cdot 10^4$ |
| Reconstituted teas | $1.4 \cdot 10^3$ |

Results show that reconstitution process does reduce the microbiological load. Temperatures applied all along the process have a lethal effect of microorganisms.

Example 20

Reconstituted material was produced in different physical shapes that provide for different kinds of applications. Specifically, the products shown in FIG. 21 are examples that allow for convenient preparation of tea infusions.

Example 21

A reconstituted product was made according to the following method: coffee (*Coffea* spp) was initially heated at 60° C. for 20 minutes with a coffee/water ratio of 1 to 5 by weight. This was followed by an extraction step in a hydraulic press to separate the aqueous portion from the coffee fiber portion. The recovered coffee fiber portion was again heated at 60° C. for 10 minutes with a coffee/water ratio of 1 to 5 by weight. After an additional extraction (by pressing), the fibrous portion was then refined in a Valley beater at 1.4% consistency for 10 minutes. After refining, cellulosic fibers (a blend of abaca, hardwood and softwood pulps, with the respective ratios: 60/10/30) were added to the coffee fibrous residue with a coffee fiber/woodpulp ratio of 5 to 1 in weight and a wet strength agent was then added to the fibrous portion at a level of 5% w/w in order to make hand sheets. The aqueous portion was concentrated in an evaporator to a solid concentration of 50% and then coated on a hand sheet on a manual size-press. In this example, the product was produced at 30% extract content, which is the soluble content of the starting material of the experiment. The coated hand sheets were dried on a plate dryer.

The product obtained in this example was tested for its properties in preparing coffee and compared to original material. Both products were used to make coffee, and the optical density of the solution (coffee) was measured at 274 nm. For all samples, the total infusion time in hot water (90° C.) was 5 minutes. Same weights of coffee material (2.5 grs) and identical experimental conditions were used: a beaker containing 500 ml water was heated at 90° C. At T=0, ie. upon start of the experiment, heating was stopped and a coffee strip was immersed into water. A rotary magnet was used to homogenize the content of the beaker during the entire experiment.

Samples of water were taken regularly and up to 5 minutes. Then, the optical density of the sample was determined using a spectrophotometer at the wavelength of 274 nm (maximum absorption of caffeine). The reference blank test was run with a sample of clear water heated at 90° C.

Figure 22:
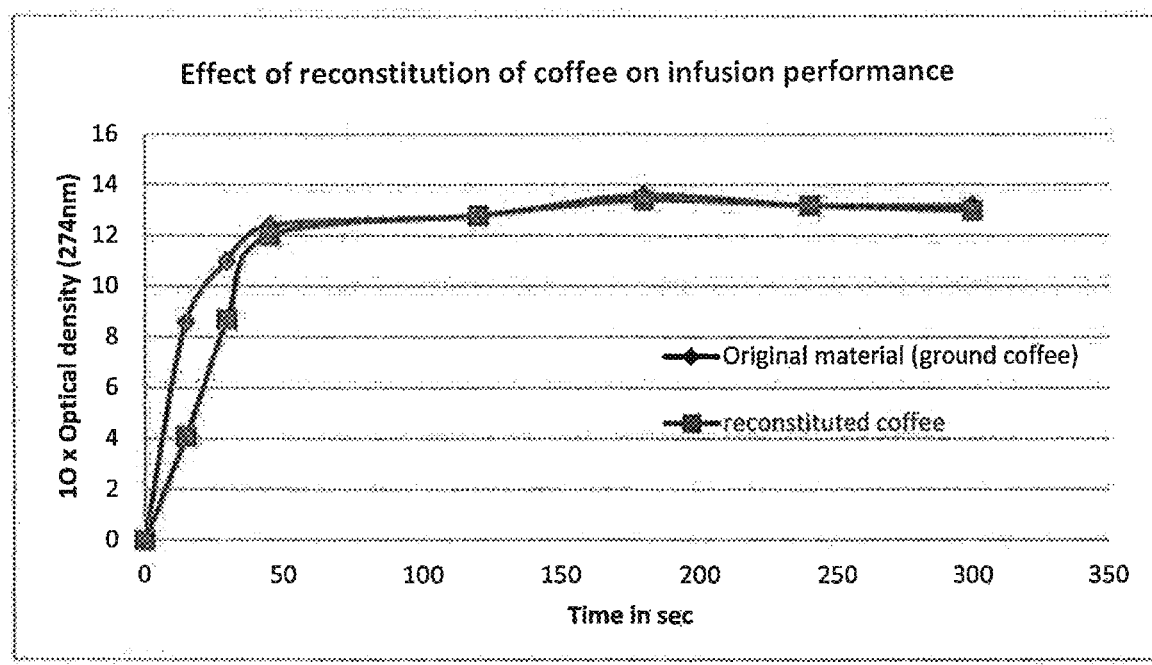
FIG. 22 shows the infusion performance of a reconstituted coffee material.

The result is graphically shown in FIG. 22 below.

While infusion prepared with original coffee material is faster during the first 50 seconds, after 1 minute, infusion profiles of both samples are similar.

Example 22

Reconstitution of Peppermint (*Mentha×Piperita*) and Green Tea Leaves (*Camellia sinensis*)

A reconstituted product was made according to the following method: Peppermint (*Mentha×piperita*) and Green Tea (*Camellia sinensis*) natural leaves were initially blended with a ratio of 50/50 and aforementioned blend was heated at 85° C. for 20 minutes with a blend/water ratio of 1 to 5 by weight. This was followed by an extraction step in a hydraulic press to separate the aqueous portion from the blend fiber portion. The blend fiber portion was again heated at 85° C. for 10 minutes with a blend/water ratio of 1 to 5 by weight. After an additional extraction (by pressing), the fibrous portion was then refined in a Valley beater at 1.4% consistency for 10 minutes. After refining, cellulosic fibers (abaca pulp) were added to the blend fibrous residue with a blend fiber/wood pulp ratio of 5 to 1 in weight. A wet strength agent was then added to the fibrous portion at a level of 5% w/w in order to make hand sheets. The aqueous portion was concentrated in an evaporator to a solid concentration of 50%. Various products were produced at different basis weights/soluble ratios. Coated hand sheets were then dried on a plate dryer.

Samples were evaluated for skin applications by a sensory panel. Products were immersed into water at room temperature for 2 seconds and later applied onto the panelists faces. Color, odor, drape (propensity to loosely place the sheet onto the face) and wet strength of the different samples were assessed.

| Sample ref. | Dry Basis weight (g/m²) | Soluble addition (w/w %) |
|---|---|---|
| 1562A1_fdb | 50 | 0 |
| 1562A1 | 80 | 37 |
| 1562A2_fdb | 70 | 0 |
| 1562A2 | 110 | 37 |
| 1562A3_fdb | 50 | 0 |
| 1562A3 | 60 | 15 |
| 1562A4_fdb | 70 | 0 |
| 1562A4 | 80 | 15 |

As expected, the higher the added extract level, the greener the samples color (from greenish to deep green for samples at 37%). All samples provide a pleasant fresh smell especially at higher levels of extract. Drape is better at lower basis weights and low levels of extracts. However, the behavior of samples with basis weights below 80 gsm is considered as acceptable for facial applications by all panelists (product evenly covers the respective area(s)). Finally, cohesiveness in wet conditions of all samples is good since the material could be manipulated several times with no noticeable tear. After 5 minutes application, a feeling of freshness on the skin was unanimously mentioned by the group of panelists.

The invention claimed is:

1. A reconstructed plant product for medicinal, cosmetic, coloring or dermatological use, the reconstructed plant product comprising an effective amount of a fibrous plant residue and a plant extract,
   wherein the fibrous plant residue comprises fibrous residue from a tea (*Camillia sinensis*) plant and the plant extract comprises at least one substance extracted from the tea plant, and
   wherein the reconstructed plant product is obtained from the following process:
   mixing one or more plant components with a solvent to form a plant extract and a fibrous plant residue;
   separating the plant extract from the fibrous plant residue and refining the fibrous residue to produce a fibrous pulp and transferring the fibrous pulp to a papermaking process to produce an insoluble paper-like sheet product;

concentrating, purifying or aromatizing the plant extract;

applying the plant extract to the insoluble paper-like sheet product; and drying the insoluble paper-like sheet product after the plant extract has been applied.

2. The product of claim 1, wherein the fibrous plant residue comprises substances from one or more specific parts of one or more plants.

3. The product of claim 1, wherein the plant extract comprises substances from one or more specific parts of one or more plants and wherein the plant extract is obtained from the fibrous plant residue.

4. The product of claim 3 for coloring use, wherein the fibrous plant residue, the plant extract, or a combination thereof comprises substances from one or more specific parts of one or more plants, and wherein the plants are selected from at least one plant for red color, brown color, black color, dark color, red color, purple color, yellow color, orange color, green color, blue color, or combinations thereof.

5. The product of claim 3, wherein the plant extract forms a layer which is located on the layer of the fibrous plant residue.

6. The product of claim 3, wherein the plant extract is at least partially penetrated into the fibrous plant residue.

7. The product of claim 3, wherein the plant extract is applied to the fibrous plant residue as a fluid, a gel, a slurry, or a powder.

8. The product of claim 3, wherein the plant extract comprises one or more substances from one or more types of plants of the fibrous plant residue.

9. The product of claim 3, wherein the fibrous plant residue, the plant extract, or a combination thereof comprises a blend of different plants.

10. The product of claim 3, wherein the fibrous plant residue comprises at least 30% by weight of a fibrous plant residue from one plant.

11. The product of claim 3, wherein the plant extract comprises at least 30% by weight of a plant extract from one plant.

12. The product of claim 3, wherein the plant extract is soluble, dispersible, or water-soluble.

13. The product of claim 1, wherein the fibrous plant residue, the plant extract, or a combination thereof comprises substances from one or more specific parts of at least a second plant, and wherein the at least second plant is selected from the group consisting of herbs, medicinal plants, tea, vegetables, dye plants, and spices.

14. The product of claim 1 for use in a method of treating a disease or disorder.

15. A medical device comprising the product of claim 1.

16. A kit of parts comprising the product of claim 1.

17. A coloring comprising the product of claim 1.

18. The coloring matter of claim 17, wherein the coloring matter is for hair coloring and is a powder or a paste.

19. A composition comprising the product of claim 1, wherein the composition is a pharmaceutical composition, a cosmetic composition, or a dermatologic composition.

20. The composition of claim 19, wherein the composition is a sheet, a powder, a cream, a slurry, a paste, a foam, a liquid, a pellet, or a granule.

21. The composition of claim 19, wherein the composition is a medicament, a bag, a mask, at least one part of a medical device, a cosmetic agent, a coloring agent, a dermatologic agent, an antibacterial agent, an antiviral agent, a fungicide agent, or a germidical agent.

22. A method of coloring a hair, the method comprising:
applying an effective amount of the product of claim 1 to the hair.

23. A method of coloring a surface, the method comprising:
applying an effective amount of the product of claim 1 to the surface.

24. A method of treating a disease or disorder, the method comprising:
administering an effective amount of the product of claim 1.

25. A method of producing the reconstructed plant product of claim 1, comprising:
mixing one or more plant components with a solvent to form a plant extract and a fibrous plant residue;

separating the plant extract from the fibrous plant residue and refining the fibrous residue to produce a fibrous pulp and transferring the fibrous pulp to a papermaking process to produce an insoluble paper-like sheet product;

concentrating, purifying or aromatizing the plant extract;

applying the plant extract to the insoluble paper-like sheet product; and drying the insoluble paper like sheet product after the plant extract has been applied.

* * * * *